US008507545B2

(12) United States Patent
Takigawa et al.

(10) Patent No.: US 8,507,545 B2
(45) Date of Patent: Aug. 13, 2013

(54) CYTOTOXIC T CELL ACTIVATOR COMPRISING EP4 AGONIST

(75) Inventors: Masahiro Takigawa, Shizuoka (JP); Naohiro Seo, Shizuoka (JP); Kenji Kabashima, Fukuoka (JP); Takayuki Maruyama, Osaka (JP); Toshiya Kanaji, Osaka (JP)

(73) Assignees: National University Corporation, Hamamatsu University School of Medicine, Hamamatsu (JP); Ono Pharmaceutical Co., Ltd., Osaka (JP)

( * ) Notice: Subject to any disclaimer, the term of this patent is extended or adjusted under 35 U.S.C. 154(b) by 651 days.

(21) Appl. No.: 12/599,194

(22) PCT Filed: May 7, 2008

(86) PCT No.: PCT/JP2008/058464
§ 371 (c)(1),
(2), (4) Date: Nov. 6, 2009

(87) PCT Pub. No.: WO2008/136519
PCT Pub. Date: Nov. 13, 2008

(65) Prior Publication Data
US 2010/0216689 A1  Aug. 26, 2010

(30) Foreign Application Priority Data
May 8, 2007  (JP) .................... 2007-123119

(51) Int. Cl.
*A61K 31/40*  (2006.01)
*A61K 31/10*  (2006.01)

(52) U.S. Cl.
USPC .......................... 514/424; 514/712

(58) Field of Classification Search
USPC ................. 514/424, 712
See application file for complete search history.

(56) References Cited

U.S. PATENT DOCUMENTS

| 6,462,081 B1* | 10/2002 | Maruyama et al. ........... 514/530 |
| 2004/0209848 A1 | 10/2004 | Maruyama |
| 2005/0003533 A1 | 1/2005 | Kalinski |
| 2006/0093617 A1* | 5/2006 | Buyse et al. ............... 424/189.1 |
| 2008/0021021 A1 | 1/2008 | Okada |
| 2008/0033033 A1 | 2/2008 | Kambe |

FOREIGN PATENT DOCUMENTS

| EP | 0891770 A1 | 1/1999 |
| EP | 1442744 A2 | 8/2004 |
| EP | 1481976 A1 | 12/2004 |
| JP | 2000-001472 A | 1/2000 |
| JP | 2007-023028 A | 2/2007 |
| WO | 0003980 A1 | 1/2000 |
| WO | 01/37877 A1 | 5/2001 |
| WO | 03009872 A1 | 2/2003 |
| WO | WO 03103604 A2 | 12/2003 |
| WO | 2004/065365 A1 | 8/2004 |
| WO | 2005012232 A2 | 2/2005 |
| WO | 2006/016689 A1 | 2/2006 |
| WO | WO 2008058766 A1 | 5/2008 |

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*
Takahashi HK, Iwagaki H, Tamura R, Katsuno G, Xue D, Sugita S, Mori S, Yoshino T, Tanaka N, Nishibori M. Differential effect of prostaglandins E1 and E2 on lipopolysaccharide-induced adhesion molecule expression on human monocytes. Eur J Pharmacol. Apr. 11, 2005;512(2-3):223-30.*
Yoshida K, Oida H, Kobayashi T, Maruyama T, Tanaka M, Katayama T, Yamaguchi K, Segi E, Tsuboyama T, Matsushita M, Ito K, Ito Y, Sugimoto Y, Ushikubi F, Ohuchida S, Kondo K, Nakamu Stimulation of bone formation and prevention of bone loss by prostaglandin E EP4 receptor activation. Proc Natl Acad Sci U S A. Apr. 2, 2002 2;99(7):4580-5.*
Krause P, Singer E, Darley PI, Klebensberger J, Groettrup M, Legler DF. Prostaglandin E2 is a key factor for monocyte-derived dendritic cell maturation: enhanced T cell stimulatory capacity despite IDO. J Leukoc Biol. Nov. 2007;82(5):1106-14. Epub Aug. 14, 2007.*
European Search Report issued Oct. 6, 2011 in corresponding European Patent Application No. 08764261.7.
Fulton Amy M et al: "Targeting prostaglandin E EP receptors to inhibit metastasis", Cancer Research, vol. 66, No. 20, Oct. 2006, pp. 9794-9797, XP000002659220, ISSN: 0008-5472.
Hale A H et al: "Effect of prostaglandins on elicitation of anti-viral cytolytic activity", Immunology Letters, Elsevier BV, NL, vol. 4, No. 3, Mar. 1, 1982, pp. 171-174, XP023690520, ISSN: 0165-2478, DOI: 10.1016/0165-2478(82)90031-1
Jonuleit Helmut et al; "Pro-inflammatory cytokines and prostaglandins induce maturation of potent immunostimulatory dendritic cells under fetal calf serum-free conditions", European J. Immunology, vol. 27, No. 12, Dec. 1997, pp. 3135-3142, XP000002659213; ISSN: 0014-2980.
Kabashima Kenji et al: "Prostaglandin E2-EP4 signaling initiates skin immune responses by promoting migration and maturation of Langerhans cells.", Nature Medicine, vol 9, No. 6, Jun. 2003, pp. 744-749, XP000002659212, ISSN: 1078-8956.
Kubo S. et al; "E-prostanoid (EP)2/EP4 receptor-dependent maturation of human monocyte-derived dendritic cells and induction of helper T2 polarization", J. Exp. Therapeutics, vol. 309, No. 3, Jun. 1, 2004, pp. 1213-1220, XP000002659216, ISSN: 0022-3565.
Mutoh Michihiro et al: "Involvement of prostaglandin E receptor subtype EP4 in colon carcinogenesis", Cancer Research, vol. 62, No. 1, Jan. 1, 2002, pp. 28-32, XP000002659218, ISSN: 0008-5472.

(Continued)

*Primary Examiner* — Paul Zarek
(74) *Attorney, Agent, or Firm* — Sughrue Mion, PLLC

(57) ABSTRACT

Disclosed is a substance which has a low molecular weight, can be applied in a simpler manner, and has an immunopotentiating activity against cancer and/or a microorganism-mediated infectious disease.
An EP4 agonist exhibits an immunopotentiating activity through the activation of a cytotoxic T cell, and is therefore useful for the prevention and/or treatment of cancer or a microorganism-mediated infection disease.

19 Claims, 1 Drawing Sheet

(56) References Cited

OTHER PUBLICATIONS

Okuyama T et al; "Activation of prostaglandin E2-receptor EP2 and EP4 pathways induces growth inhibition in human gastric carcinoma cell lines", Journal of Laboratory and Clinical Medicine, vol. 140, No. 2, Aug. 2002, pp. 92-102, XP000002659215, ISSN: 0022-2143.

Rubio M. T et al: "Maturation of human monocyte-derived dendritic cells (MoDCs) in the presence of prostaglandin E2 optimizes CD4 and CD8 T cell-mediated reponses to protein antigens: role of PGE2 in chemokine and cytokine expression by MoDCs", Int. Immuno., GB, vol. 17, No. 12, Dec. 1, 2005, pp. 1561-1572, XP002520632, ISSN: 0953-8178.

Seo et al:, "The current status and future direction of percutaneous peptide immunization against melanoma", Journal of Dermatological Science, vol. 48, No. 2, Sep. 14, 2007, pp. 77-85, XP022243669, ISSN: 0923-1811.

Seo N et al: "Percutaneous peptide immunization via corneum barrier-disrupted murine skin for experimental tumor immunoprophylaxis", PNAS, Washington, DC; US, vol. 97, No. 1, Jan. 4, 2000, pp. 371-376; XP002272394, ISSN 0027-8424.

Steinbrink Kerstin et al; "Induction of dendritic cell maturation and modulation of dendritic cell-induced immune responses by prostaglandins", Archives of Dermatological Research, vol. 292, No. 9, Sep. 2000, pp. 437-445, XP000002659214, ISSN: 0340-3696.

Tanaka Fumiaki et al: "Efficient induction of specific cytotoxic T lymphocytes to tumor rejection peptide using functional matured 2 day-cultured dendritic cells derived from human monocytes", Int. J. Oncology, vol. 29, No. 5, Nov. 2006, pp. 1263-1268, XP000002659211, ISSN: 1019-6439.

Yagi Hiroaki et al; "Induction of therapeutically relevant cytotoxic T lymphocytes in humans by percutaneous peptide immunization", Cancer Research, vol. 66, No. 20, Oct. 2006, pp. 10136-10144, XP002659834, ISSN: 0008-5472.

Yang Li et al: "Host and direct antitumor effects and profound reduction in tumor metastasis with selective EP4 receptor antagonism", Cancer Research, vol. 66, No. 19, Oct. 2006, pp. 9665-9672, XP000002659219, ISSN: 00085472.

Office Action dated Oct. 21, 2010, issued in corresponding New Zealand Patent Application No. 581006.

International Search Report [PCT/ISA/210] for PCT/JP2008/058464, dated Aug. 5, 2008.

\* cited by examiner

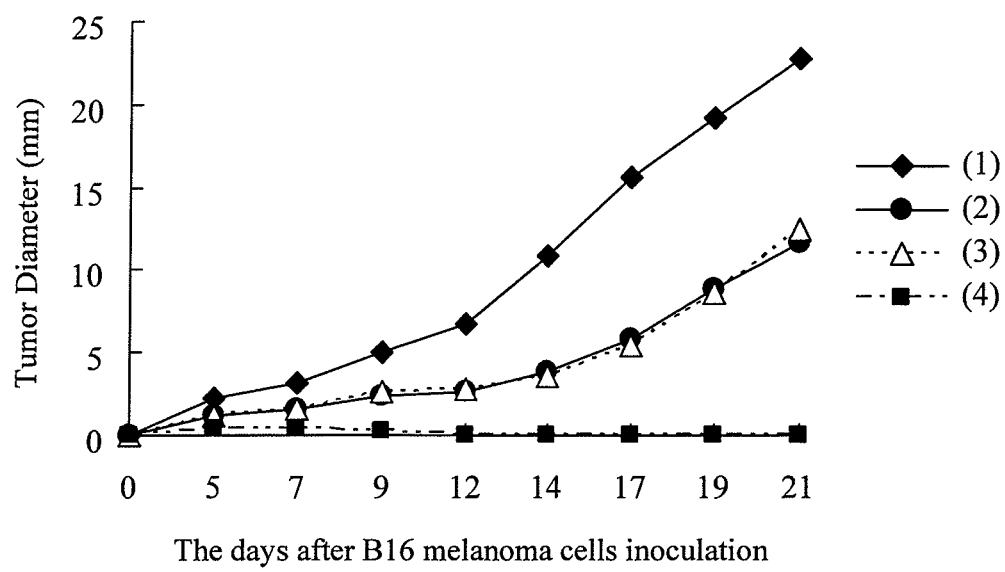

```
SEQUENCE LISTING

<160> NUMBER OF SEQ ID NOS: 2

<210> SEQ ID NO 1
<211> LENGTH: 8
<212> TYPE: PRT
<213> ORGANISM: Artificial sequence
<220> FEATURE:
<223> OTHER INFORMATION: Tyrosinase-related protein 2 residues 181-188

<400> SEQUENCE: 1

Val Tyr Asp Phe Phe Val Trp Leu
 1               5

<210> SEQ ID NO 2
<211> LENGTH: 8
<212> TYPE: PRT
<213> ORGANISM: Artificial sequence
<220> FEATURE:
<223> OTHER INFORMATION: Herpes Simplex Virus glycoprotein B 498-505

<400> SEQUENCE: 2

Ser Ser Ile Glu Phe Ala Arg Leu
 1               5
```

CYTOTOXIC T CELL ACTIVATOR COMPRISING EP4 AGONIST

TECHNICAL FIELD

The present invention relates to an activator of cytotoxic T cells comprising an EP4 agonist.

More specifically, the present invention relates to an immunopotentiator via cytotoxic T cell activation comprising an EP4 agonist, particularly to an immunopotentiator for a cancer and/or a microbial infectious disease.

BACKGROUND ART

Conventional therapeutic methods for cancers include surgical therapy, chemotherapy with anticancer agents, radiotherapy, and therapeutic methods comprising a combination thereof. However, these methods are known to pose problems, including the inability to cope with cancer cell metastasis by surgical procedures, and attacking not only cancer cells, but also normal cells, to cause severe adverse effects and resistance to chemotherapy and radiotherapy as supplements to surgical procedures.

Amid this situation, investigations have recently been conducted on therapeutic methods for eliminating cancer cells by enhancing the immune system that is intrinsically present in the living organism, as a new therapeutic method for cancers. For example, clinical investigations using non-specific immunity activators (e.g., Krestin, Bestatin and the like), cytokine therapies (e.g., interferons, interleukins and the like), antibody therapies (e.g., Herceptin and the like), immune cell therapies (e.g., dendritic cell vaccine therapy, peptide vaccine therapy and the like) and the like are being conducted. In particular, an immune cell therapy aiming at activating cytotoxic T cells (Cytotoxic T lymphocyte: CTL) has recently been attracting attention. In that method, immature T cells recognize a complex of a major histocompatibility complex (MHC) molecule and an antigen peptide (e.g., fragmented cancer cell antigens and the like) presented by antigen-presenting cells (e.g., dendritic cells, macrophages and the like); at the same time a signal comes from a co-stimulatory molecule, whereby the immature T cells are induced to mature T cells exhibiting specific cytotoxicity for the presented complex, i.e., CTL. Dendritic cell vaccine therapy is a method wherein CTLs are efficiently induced by administering antigen-presented dendritic cells in culture, but problems such as those related to the use of a culture broth containing fetal calf serum and the route of administration are of concern. Peptide vaccine therapy is a method wherein an antigen peptide(s) derived from an inactivated cancer cell or a microorganism-infected cell is administered to promote the activation of CTLs that specifically recognize the antigen. Furthermore, with the use of an inactivated virus fragment or a microbial peptide such as protozoan peptide as the antigen peptides, immune cell therapies are applied not only to cancers, but also to microbial infectious diseases.

To date, more efficient and safer immune cell therapies comprising a combination thereof have been developed. For example, a method of transdermal immunotherapy has been developed wherein a corneal layer is removed using a highly adhesive tape to activate epidermal Langerhans cells, a type of dendritic cell, and antigen peptides are applied to the skin thus deprived of the corneal layer to induce CTLs in the living organism (see Patent Document 1 and Non-patent Documents 1 and 2).

Meanwhile, it is known that EP4 agonists, which bind specifically to EP4 receptor, subtype of PGE2 receptors, directly inhibit the proliferation of gastric cancer cells (see Non-patent Document 3), promote the maturation and migration of epidermal Langerhans cells being antigen-presenting cells to mediate the exacerbation of contact dermatitis (see Non-patent Document 4), and are useful as a therapeutic agent for autoimmune diseases such as rheumatism (see Patent Document 2). It is also known that EP4 antagonists are useful in the prevention and/or treatment of cancers (carcinogenesis, cancer growth, cancer visceral metastasis, cancer bone metastasis, hypercalcemia induced by cancer bone metastasis, and the like) (see Patent Document 3).

However, these documents do not state or suggest that EP4 agonists exhibit immunopotentiation via activation of cytotoxic T cells, particularly that EP4 agonists alone are useful in cancers (particularly melanoma), viral infections and the like on the basis of this immunopotentiating action.

[Patent Reference 1] Japanese Patent No. 3879785

[Patent Reference 2] International Publication No. 2003/009872

[Patent Reference 3] International Publication No. 01/062708

[Non Patent Reference 1] Proceedings of the natural academy sciences of USA, Vol. 97, 371-376, 2000

[Non Patent Reference 2] Cancer research, Vol. 66, 10136-10144, 2006

[Non Patent Reference 3] The journal of laboratory and clinical medicine, Vol. 140, 92-102, 2002

[Non Patent Reference 4] Nature medicine, Vol. 9, 744-749, 2003

DISCLOSURE OF THE INVENTION

Problems that the Invention is to Solve

So far, attempts have been made to utilize immune cell therapies as a therapeutic method for cancers or infectious diseases; for example, however, the therapies have not yet been established as an effective therapeutic method because the antigen peptides used therein are problematic in terms of efficacy and method of administration, and the dendritic cells used are problematic in terms of safety. Accordingly, it is an object of the present invention to provide a drug that potenciates immunity against cancers, viruses and the like via activation of cytotoxic T cells, is also applicable as an adjuvant, is of low molecular weight, is safer, and is conveniently applicable.

Means for Solving the Problems

The present inventors diligently investigated to accomplish the above-described object, and surprisingly found that EP4 agonists (1) activate cytotoxic T cells, (2) exhibit immunopotentiating action via the activation of cytotoxic T cells, and particularly (3) exhibit immunopotentiation against cancers and/or microbial infectious diseases, and have developed the present invention.

That is, the present invention relates to

[1] an agent for cytotoxic T cell activation comprising EP4 agonist,

[2] the agent according to the above-mentioned [1], wherein the EP4 agonist is a compound represented by formula (I)

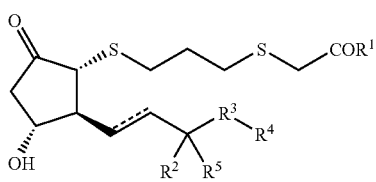

(I)

wherein R¹ is hydroxyl, C1-6 alkyloxy or NR⁶R⁷, wherein R⁶ and R⁷ are each independently hydrogen atom or C1-6 alkyl;
R² is hydrogen atom or hydroxyl;
R³ is a bond or C1-6 alkylene;
R⁴ is
(i) C1-8 alkyl, C2-8 alkenyl or C2-8 alkynyl substituted by 1 to 3 substituent(s) selected from C1-6 alkyloxy and halogen atom(s),
(ii) phenyloxy or C3-7 cycloalkyloxy,
(iii) furyl, furyloxy, thienyl, thienyloxy, naphthyl, naphthyloxy, phthalanyl or phthalanyloxy,
(iv) phenyl, phenyloxy, C3-7 cycloalkyl or C3-7 cycloalkyloxy substituted by 1 to 3 substituent(s) selected from the following groups:
(1) C1-6 alkyl, (2) C2-6 alkenyl, (3) C2-6 alkynyl, (4) C1-6 alkyloxy, (5) C1-6 alkyloxy-C1-6 alkyl, (6) C1-6 alkyloxy-C1-6 alkyloxy, (7) C2-6 alkenyloxy-C1-6 alkyl, (8) C1-6 alkyl substituted by 1 to 3 hydroxy, (9) C1-6 alkyl substituted by 1 to 3 halogen atom(s), (10) C1-6 alkylthio, (11) C1-6 alkylthio-C1-6 alkyl, (12) C1-6 alkylthio-C1-6 alkyloxy, (13) C2-6 alkenylthio-C1-6 alkyl, (14) C1-6 alkylsulfonyl, (15) halogen atom, (16) trihalomethyl, (17) cyano, (18) nitro, (19) amino, (20) hydroxy, (21) C3-7 cycloalkyl, (22) C3-7 cycloalkyloxy, (23) C3-7 cycloalkyl-C1-6 alkyl, (24) C3-7 cycloalkyloxy-C1-6 alkyl, (25) phenyl, (26) phenyloxy, (27) phenyl-C1-6 alkyl, (28) phenyl-C2-6 alkenyl, (29) phenyl-C2-6 alkynyl, (30) phenyloxy-C1-6 alkyl, (31) phenyloxy-C2-6 alkenyl, (32) phenyloxy-C2-6 alkynyl, (33) furyl, (34) furyloxy, (35) furyl-C1-6 alkyl, (36) furyloxy-C1-6 alkyl, (37) thienyl, (38) thienyloxy, (39) thienyl-C1-6 alkyl or (40) thienyloxy-C1-6 alkyl, wherein the above mentioned phenyl, furyl, thienyl and cycloalkyl are optionally substituted by 1 to 3 substituent(s) selected from C1-6 alkyl, C1-6 alkyloxy, C1-6 alkyloxy-C1-6 alkyl, nitro, halogen, trihalomethyl, amino and hydroxyl;
or
(v) furyl, furyloxy, thienyl, thienyloxy, naphthyl, naphthyloxy, phthalanyl or phthalanyloxy substituted by 1 to 3 substituent(s) selected from the following groups:
(1) C1-6 alkyl, (2) C2-6 alkenyl, (3) C2-6 alkynyl, (4) C1-6 alkyloxy, (5) C1-6 alkyloxy-C1-6 alkyl, (6) C1-6 alkyloxy-C1-6 alkyloxy, (7) C2-6 alkenyloxy-C1-6 alkyl, (8) C1-6 alkyl substituted by 1 to 3 hydroxy, (9) C1-6 alkyl substituted by 1 to 3 halogen atom(s), (10) C1-6 alkylthio, (11) C1-6 alkylthio-C1-6 alkyl, (12) C1-6 alkylthio-C1-6 alkyloxy, (13) C2-6 alkenylthio-C1-6 alkyl, (14) C1-6 alkylsulfonyl, (15) halogen atom, (16) trihalomethyl, (17) cyano, (18) nitro, (19) amino, (20) hydroxy, (21) C3-7 cycloalkyl, (22) C3-7 cycloalkyloxy, (23) C3-7 cycloalkyl-C1-6 alkyl, (24) C3-7 cycloalkyloxy-C1-6 alkyl, (25) phenyl, (26) phenyloxy, (27) phenyl-C1-6 alkyl, (28) phenyl-C2-6 alkenyl, (29) phenyl-C2-6 alkynyl, (30) phenyloxy-C1-6 alkyl, (31) phenyloxy-C2-6 alkenyl, (32) phenyloxy-C2-6 alkynyl, (33) furyl, (34) furyloxy, (35) furyl-C1-6 alkyl, (36) furyloxy-C1-6 alkyl, (37) thienyl, (38) thienyloxy, (39) thienyl-C1-6 alkyl or (40) thienyloxy-C1-6 alkyl, wherein the above mentioned phenyl, furyl, thienyl and cycloalkyl being optionally substituted by 1 to 3 substituent(s) selected from C1-6 alkyl, C1-6 alkyloxy, C1-6 alkyloxy-C1-6 alkyl, nitro, halogen, trihalomethyl, amino and hydroxyl;

R⁵ is hydrogen atom or C1-6 alkyl;

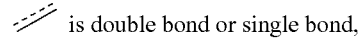 is double bond or single bond, with the proviso that R² is hydrogen atom, C1-6 alkylene represented by R³ may be substituted by one hydroxy, a mixture of 8-epi compound which is an equilibrium compound thereof, a non toxic salt thereof or a cyclodextrin clathrate thereof, a compound represented by formula (IL)

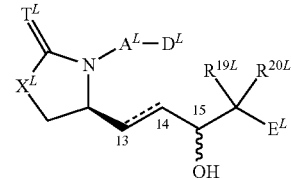

(IL)

wherein $\approx$ is (1) single bond or (2) double bond, $R^{19L}$ and $R^{20L}$ are each independently, (1) hydrogen atom, (2) C1-10 alkyl or (3) halogen atom, $T^L$ is (1) oxygen atom or (2) sulfur atom, $X^L$ is (1) —$CH_2$—, (2) —O— or (3) —S—, $A^L$ is $A^{1L}$ or $A^{2L}$, $A^{1L}$ is (1) C2-8 straight-chain alkylene optionally substituted by 1 to 2 C1-4 alkyl, (2) C2-8 straight-chain alkenylene optionally substituted by 1 to 2 C1-4 alkyl or (3) C2-8 straight-chain alkynylene optionally substituted by 1 to 2 C1-4 alkyl, $A^{2L}$ is -$G^{1L}$-$G^{2L}$-$G^{3L}$-, $G^{1L}$ is (1) C1-4 straight-chain alkylene optionally substituted by 1 to 2 C1-4 alkyl, (2) C2-4 straight-chain alkenylene optionally substituted by 1 to 2 C1-4 alkyl or (3) C2-4 straight-chain alkynylene optionally substituted by 1 to 2 C1-4 alkyl, $G^{2L}$ is (1) —$Y^L$—, (2) -(ring$1^L$)-, (3) —$Y^L$—(ring$1^L$)-, (4) -(ring$1^L$)-$Y^L$— or (5) —$Y^L$—(C1-4 alkylene)-(ring$1^L$)-, $Y^L$ is (1) —S—, (2) —SO—, (3) —$SO_2$—, (4) —O— or (5) —$NR^{1L}$—, $R^{1L}$ is (1) hydrogen atom, (2) C1-10 alkyl or (3) C2-10 acyl, $G^{3L}$ is (1) bond, (2) C1-4 straight-chain alkylene optionally substituted by 1 to 2 C1-4 alkyl, (3) C2-4 straight-chain alkenylene optionally substituted by 1 to 2 C1-4 alkyl or (4) C2-4 straight-chain alkynylene optionally substituted by 1 to 2 C1-4 alkyl, $D^L$ is $D^{1L}$ or $D^{2L}$, $D^{1L}$ is (1) —COOH, (2) —$COOR^{2L}$, (3) tetrazol-5-yl or (4) $CONR^{3L}SO_2R^{4L}$, $R^{2L}$ is (1) C1-10 alkyl, (2) phenyl, (3) C1-10 alkyl substituted by phenyl or (4) biphenyl, $R^{3L}$ is (1) hydrogen atom or (2) C1-10 alkyl, $R^{4L}$ is (1) C1-10 alkyl or (2) phenyl, $D^{2L}$ is (1) —$CH_2OH$, (2) —$CH_2OR^{5L}$, (3) hydroxy, (4) —$OR^{5L}$, (5) formyl, (6) —$CONR^{6L}R^{7L}$, (7) —$CONR^{6L}SO_2R^{8L}$, (8) —CO—(NH-amino acid residue-CO)$_{mL}$—OH, (9) —O—(CO— amino acid residue —NH)$_{mL}$—H, (10) —$COOR^{9L}$, (11) —OCO—$R^{10L}$, (12) —COO—$Z^{1L}$—$Z^{2L}$—$Z^{3L}$, (13)

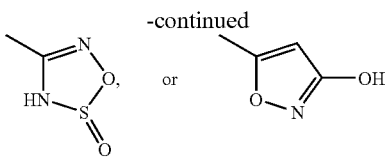

$R^{5L}$ is C1-10 alkyl, $R^{6L}$ and $R^{7L}$ are each independently, (1) hydrogen atom or (2) C1-10 alkyl, $R^{8L}$ is C1-10 alkyl substituted by phenyl, $R^{9L}$ is (1) C1-10 alkyl substituted by biphenyl optionally substituted by 1 to 3 C1-10 alkyl, C1-10 alkoxy or halogen atom or (2) biphenyl substituted by 1 to 3 C1-10 alkyl, C1-10 alkoxy or halogen atom(s), $R^{10L}$ is (1) phenyl or (2) C1-10 alkyl, mL is 1 or 2, $Z^{1L}$ is (1) C1-15 alkylene, (2) C2-15 alkenylene or (3) C2-15 alkynylene, $Z^{2L}$ is (1) —CO—, (2) -OOO-, (3) —COO—, (4) —CONR$^{11L}$—, (5) —NR$^{12L}$CO—, (6) —O—, (7) —S—, (8) —SO—, (9) —SO$_2$—, (10) —NR$^{13L}$—, (11) —NR$^{14L}$CONR$^{15L}$—, (12) —NR$^{16L}$COO—, (13) —OCONR$^{17L}$— or (14) —OCO—, $Z^{3L}$ is (1) hydrogen atom, (2) C1-15 alkyl, (3) C2-15 alkenyl, (4) C2-15 alkynyl, (5) ring$2^L$ or (6) C1-10 alkyl substituted by C1-10 alkoxy, C1-10 alkylthio, C1-10 alkyl-NR$^{18L}$— or ring$2^L$, $R^{11L}$, $R^{12L}$, $R^{13L}$, $R^{14L}$, $R^{15L}$, $R^{16L}$, $R^{17L}$ and $R^{18L}$ are each independently (1) hydrogen atom or (2) C1-15 alkyl, $R^{11L}$ and $Z^{3L}$ may be taken together with the nitrogen atom to which they are attached to form 5 to 7 membered saturated mono-heterocyclic ring, and the heterocyclic ring may contain another one hetero atom selected from oxygen, nitrogen and sulfur atom, $E^L$ is $E^{1L}$ or $E^{2L}$, $E^{1L}$ is (1) C3-7 cycloalkyl or (2) ring$3^L$, $E^{2L}$ is (1) C3-7 cycloalkyl, (2) ring$4^L$ or (3) ring$5^L$, ring$1^L$ and ring$5^L$ are optionally substituted by 1 to 3 $R^{21L}$ and/or $R^{22L}$, ring$3^L$ is optionally substituted by 1 to 2 $R^{21L}$, C3-7 cycloalkyl represented by $E^{2L}$ is substituted by one of $R^{21L}$ or $R^{22L}$, and optionally substituted by other 1 to 2 $R^{21L}$ and/or $R^{22L}$, ring$4^L$ is substituted by one of $R^{22L}$, optionally substituted by other 1 to 2 $R^{21L}$ and/or $R^{22L}$, and heterocyclic ring formed by $R^{11L}$, $Z^{3L}$ and the nitrogen to which $Z^{3L}$ is attached or ring$2^L$ may be substituted by $R^{23L}$, $R^{21L}$ is (1) C1-10 alkyl, (2) C1-10 alkoxy, (3) halogen atom, (4) nitro, (5) C1-10 alkyl substituted by 1 to 3 halogen atom(s) or (6) phenyl, $R^{22L}$ is (1) C2-10 alkenyl, (2) C2-10 alkynyl, (3) C1-10 alkylthio, (4) hydroxy, (5) —NR$^{24L}$R$^{25L}$, (6) C1-10 alkyl substituted by C1-10 alkoxy, (7) C1-10 alkyl substituted by C1-10 alkoxy substituted by 1 to 3 halogen atom(s), (8) C1-10 alkyl substituted by —NR$^{24L}$R$^{25L}$, (9) ring$6^L$, (10) —O-ring$7^L$, (11) C1-10 alkyl substituted by ring$7^L$, (12) C2-10 alkenyl substituted by ring$7^L$, (13) C2-10 alkynyl substituted by ring$7^L$, (14) C1-10 alkoxy substituted by ring$7^L$, (15) C1-10 alkyl substituted by —O-ring$7^L$, (16) —COOR$^{26L}$ or (17) C1-10 alkoxy substituted by 1 to 3 halogen atom(s), $R^{24L}$, $R^{25L}$ and $R^{26L}$ are each independently, (1) hydrogen atom or (2) C1-10 alkyl, $R^{23L}$ is (1) C1-15 alkyl, (2) C2-15 alkenyl, (3) C2-15 alkynyl or (4) C1-10 alkyl substituted by C1-10 alkoxy, C1-10 alkylthio or C1-10 alkyl-NR$^{27L}$—, $R^{27L}$ is (1) hydrogen atom or (2) C1-10 alkyl, ring$1^L$, ring$2^L$, ring$5^L$, ring$6^L$ and ring$7^L$ are (1) C3-15 mono-, bi- or tri-carbocyclic aryl which may be partially or fully saturated or (2) 3 to 15 membered mono-, bi- or tri-heterocyclic aryl containing 1 to 4 hetero atom(s) selected from oxygen, nitrogen and sulfur atom(s) which may be partially or fully saturated, ring$3^L$ and ring$4^L$ are (1) thienyl, (2) phenyl or (3) furyl, ring$6^L$ and ring$7^L$ may be substituted by 1 to 3 $R^{28L}$, $R^{28L}$ is (1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1 to 3 halogen atom(s) or (9) C1-10 alkyl substituted by C1-10 alkoxy substituted by 1 to 3 halogen atom(s), a salt thereof, an N-oxide thereof or a solvate thereof, or a prodrug thereof, or a cyclodextrin clathrate thereof, or
a compound represented by formula (IM)

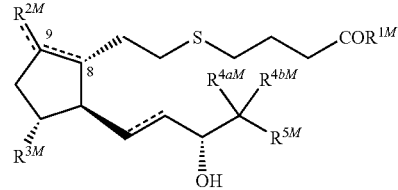

(IM)

wherein $R^{1M}$ is hydroxy, C1-6 alkyloxy or NR$^{6M}$R$^{7M}$, wherein $R^{6M}$ and $R^{7B}$ are each independently hydrogen or C1-4 alkyl, $R^{2M}$ is oxygen atom, halogen atom or O—COR$^{8M}$, wherein $R^{8M}$ is C1-4 alkyl, phenyl or phenyl (C1-4 alkyl)), $R^{3M}$ is hydrogen atom or hydroxy, $R^{4aM}$ and $R^{4bM}$ are each independently hydrogen atom or C1-4 alkyl, $R^{5M}$ is phenyl substituted with the following substituent(s):
i) 1 to 3 selected from (a) C1-4 alkyloxy-C1-4 alkyl, (b) C2-4 alkenyloxy-C1-4 alkyl, (c) C2-4 alkynyloxy-C1-4 alkyl, (d) C3-7 cycloalkyloxy-C1-4 alkyl, (e) C3-7 cycloalkyl(C1-4 alkyloxy)-C1-4 alkyl, (f) phenyloxy-C1-4 alkyl, (g) phenyl-C1-4 alkyloxy-C1-4 alkyl, (h) C1-4 alkylthio-C1-4 alkyl, (i) C2-4 alkenylthio-C1-4 alkyl, (j) C2-4 alkynylthio-C1-4 alkyl, (k) C3-7 cycloalkylthio-C1-4 alkyl, (l) C3-7 cycloalkyl(C1-4 alkylthio)-C1-4 alkyl, (m) phenylthio-C1-4alkyl and (n) phenyl-C1-4 alkylthio-C1-4 alkyl,
ii) (a) C1-4 alkyloxy-C1-4 alkyl and C1-4 alkyl, (b) C1-4 alkyloxy-C1-4 alkyl and C1-4 alkyloxy, (c) C1-4 alkyloxy-C1-4 alkyl and hydroxy, (d) C1-4 alkyloxy-C1-4 alkyl and halogen atom, (e) C1-4 alkylthio-C1-4 alkyl and C1-4 alkyl, (f) C1-4 alkylthio-C1-4 alkyl and C1-4 alkyloxy, (g) C1-4 alkylthio-C1-4 alkyl and hydroxy or (h) C1-4 alkylthio-C1-4 alkyl and halogen atom,
iii) (a) haloalkyl or (b) hydroxy-C1-4 alkyl, or
iv) C1-4 alkyl and hydroxy;

is single bond or double bond, and it is not double bond continuously,
a salt thereof, an N-oxide thereof or a solvate thereof, or a prodrug thereof, or a cyclodextrin clathrate thereof,
[3] the agent according to the above-mentioned [1], wherein the cytotoxic T cell activation is potentiation of immunity against a cancer and/or microbial infectious disease,
[4] the agent according to the above-mentioned [3], wherein the cancer is one or more selected from among a digestive cancer, a skin cancer, a respiratory cancer, a urinary cancer, a liver cancer, and a pancreatic cancer,
[5] the agent according to the above-mentioned [4], wherein the skin cancer is a melanoma,
[6] the agent according to the above-mentioned [3], wherein the microorganism is one or more selected from among a virus, a bacterium, and a fungus,
[7] the agent according to the above-mentioned [1], wherein EP4 agonist is 11α,15α,-dihydroxy-9-oxo-16-(3-methoxymethylphenyl)-17,18,19,20-tetranor-3,7-ditiaprost-13E-enoic acid, 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butaniic acid or methyl 4-{[2-((1R,2R, 3R)-3-hydroxy-2-{(1E,3S)-3-hydroxy-4-[3-(methoxymethyl)phenyl]but-1-enyl}-5-oxocyclopentyl)ethyl]sulfanyl}butanoate,

[8] the agent according to the above-mentioned [1], wherein the agent further comprises an antigen peptide(s),

[9] the agent according to the above-mentioned [8], wherein the antigen peptide(s) is a melanoma-specific antigen peptide,

[10] a pharmaceutical to be administered to a skin deprived of the corneal layer to potentiate immunity against a cancer with a low prevalence of adverse effects, comprising 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[24(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid, or methyl 4-{[24(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate as an active ingredient,

[11] the pharmaceutical according to the above-mentioned [10], wherein the cancer is melanoma,

[12] the pharmaceutical according to the above-mentioned [10], wherein the pharmaceutical further comprises an antigen peptide(s),

[13] the pharmaceutical according to the above-mentioned [12], wherein the antigen peptide(s) is a melanoma-specific antigen peptide, and the cancer is melanoma,

[14] a method for activating cytotoxic T cells in a mammal, comprising administering an effective amount of EP4 agonist to the mammal,

[15] use of EP4 agonist for producing an activator of cytotoxic T cells, and

[16] EP4 agonist for activating cytotoxic T cells.

The Effect of the Invention

EP4 agonists alone exhibit immunopotentiation via activation of cytotoxic T cells. For this reason, these agonists are useful in the prevention and/or treatment of cancers, microbial infectious diseases and the like. Furthermore, by using the agonists in combination with antigen peptides, an adjuvant effect can also be obtained.

BEST MODE FOR CARRYING OUT THE INVENTION

In the present invention, as shown in Examples below, EP4 agonists alone activate cytotoxic T cells (Cytotoxic T lymphocyte: hereinafter sometimes abbreviated CTLs), and can therefore be used alone as an activator of cytotoxic T cells.

In the present invention, CTLs mean T cells, also known as killer T cells, which express the CD8 molecule on the surfaces thereof. Generally, immature T cells strongly bind to antigens (e.g., cancer cell-specific peptides, virus-specific peptides) presented onto a major histocompatibility complex (MHC) molecule by antigen-presenting cells (e.g., macrophages, dendritic cells (e.g., follicular dendritic cells, lymphatic tissue dendritic cells, interconnecting cells, Langerhans cells, thymic dendritic cells and the like) and the like), after which the T cells are activated as antigen-specific CTLs.

In the present invention, activation of cytotoxic T cells means a quantitative increase in CTLs themselves and qualitative hyperfunction associated with cytotoxicity. For example, these include promotion of division and proliferation of CTLs in lymph nodes, promotion of differentiation or maturation into CTLs, promotion of systemic circulation of CTLs via the bloodstream, promotion of migration of CTLs to portions where foreign matter has entered, and the like; two or more of these actions may be simultaneously manifested. Preference is given to promotion of division and proliferation of CTLs in lymph nodes and promotion of differentiation or maturation into CTLs. The CTLs to be activated are preferably CTLs that are specific for an antigen of target cells (e.g., cancer cells, virus-infected cells); examples include CTLs specific for the melanoma antigen TRP-2 and CTLs specific for the herpes simplex virus antigen HSVgpB.

In the present invention, immunopotentiation means that an action to eliminate target cells infected by enemies (e.g., cancer cells, pathogenic microorganisms and the like) is enhanced on the basis of activation of CTLs. Examples of indications that can be prevented and/or treated by such immunopotentiation include cancers, microbial infectious diseases and the like, cancers being suitable.

In the present invention, cancers that can be prevented and/or treated by immunopotentiation include all of what are generally called malignant tumors; examples include cancers involving cranial nerves (e.g., pediatric brain tumors (e.g., neuroblastoma, medulloblastoma, astrocytoma (juvenile piloid astrocytoma), ependymoma, craniopharyngeoma, germinoma, optic nerve glioma, choroid plexus papilloma, brain stem glioma), adult brain tumors (e.g., adult astrocytoma, adult malignant astrocytoma, adult glioblastoma, adult cerebral ventricular ependymoma, adult malignant cerebral ventricular ependymoma, adult malignant oligodendrocytoma, adult medulloblastoma, adult meningioma, adult malignant meningioma), gliomas (e.g., astrocytoma, oligodendroglioma, ependymoma, brain stem glioma), pituitary adenoma, acoustic schwannoma, retinoblastoma, uveal malignant melanoma and the like), respiratory cancers (e.g., pharyngeal cancers (e.g., epipharyngeal cancer, mesopharyngeal cancer, hypopharyngeal cancer), laryngeal cancer, paranasal sinus cancer, lung cancers (e.g., small-cell cancer, non-small-cell cancer), thymoma, mesothelioma and the like), digestive cancers (e.g., esophageal cancer, gastric cancer, duodenal cancer, colorectal cancers (e.g., colic cancer, rectal cancer, anal cancer) and the like), oral cancers (e.g., gingival cancer, lingual cancer, salivary gland cancer and the like), urogenital cancers (e.g., penile cancer, pelvic-urethral cancer, renal cell carcinoma, testicular (orchis) tumor, prostatic cancer, urinary bladder cancer and the like), female-specific cancers (vulvar cancer, uterine cancers (e.g., uterine cervical cancer, uterine body cancer (uterine intimal cancer)), uterine sarcoma, villous diseases (e.g., hydatid moles, choriocarcinoma, placental villous tumor, persistent trophoblastic disease), vaginal cancer, breast cancer, breast sarcoma, ovarian cancer, ovarian germinoma and the like), skin cancers (e.g., melanomas (malignant melanomas) (e.g., malignant lentigo melanoma, superficial spreading melanoma, nodular melanoma, acral lentigenous melanoma, erosive melanoma), mycosis fungoides, squamous cell carcinoma, basal cell carcinoma, skin cancer prodromes/intraepidermal carcinomas (e.g., actinic keratosis, Bowen's disease, Paget's disease), lymphomatoid papulosis, dermal CD30-positive anaplastic large-cell lymphoma, Sézary syndrome, dermal B cell lymphoma and the like), bone/muscular cancers (e.g., osteosarcoma, sarcoma of soft parts, rhabdomyosarcoma, synovial sarcoma, liposarcoma and the like), thyroid cancer, carcinoid, liver cancer (hepatoma), hepatoblastoma, cholangioma, gallbladder cancer, pancreatic cancer, pancreatic endocrine tumors (e.g., insulinoma, gastrinoma, VIP-producing adenoma and the like), cancers of unknown origin, hereditary tumors/familial tumors (e.g., hereditary non-polyposis colorectal cancer, familial colorectal polyposis, hereditary breast cancer, ovarian cancer syndrome, Li-Fraumeni syndrome, hereditary melanoma, Wilms' tumor, hereditary papillary renal cell carcinoma, von Hippel-Lindau syndrome, multiple endocrine oncosis and the like), leukemias (e.g., acute myelocytic leukemia, acute lymphocytic leukemia, osteomyelodysplasia syndrome, chronic myelocytic leukemia/chronic myeloproliferative disease, adult T cell leukemia lymphoma, chronic lymphocytic leukemia/small-cell lymphoma and the like), multiple myeloma, primary macroglobulinemia, malignant lymphomas (e.g., Hodgkin's lymphoma, moderately or highly malignant lymphoma, Burkitt's lymphoma, lymphoblastic lymphoma, follicular lymphoma, mantle cell lymphoma, MALT (Mucosa-Associated Lymphoid Tissue) lymphoma, NK (natural killer) cell lymphoma and the like) and the like. Cancers that can be prevented and/or treated by immunopotentiation suitably include digestive cancers, skin cancers, respiratory cancers, urinary cancers, liver cancers, and pancreatic cancers, skin cancers being more suitable, and melanomas being particularly suitable.

In the present invention, microbial infectious diseases that can be prevented and/or treated by immunopotentiation include all of what are generally called infectious diseases, and are specifically represented by symptoms that develop as a result of proliferation of normal cells in the body infected by one or more kinds of pathogenic microorganisms, viruses, bacteria, fungi and the like. These pathogenic microorganisms also include rickettsia, chlamydia, protozoans, parasites and the like.

In the present invention, examples of viruses involved in microbial infectious diseases include human hepatitis viruses (e.g., hepatitis B, hepatitis C, hepatitis A, hepatitis E and the like), human retroviruses, human immunodeficiency viruses (e.g., HIV1, HIV2 and the like), human T cell leukemia viruses or human T lymph-oriented viruses (e.g., HTLV1, HTLV2 and the like), herpes simplex virus type 1 or type 2, Epstein-Barr (EB) virus, cytomegalovirus, varicella-zoster virus, human herpes viruses (e.g., human herpes virus 6 and the like), poliovirus, measles virus, rubella virus, Japanese encephalitis virus, mumps virus, influenza viruses, cold viruses (e.g., adenovirus, enterovirus, rhinovirus and the like), viruses that cause severe acute respiratory syndrome (SARS), Ebola virus, West Nile virus, flavivirus, echovirus, Coxsackievirus, coronavirus, respiratory coenocytic (syncytial) virus, rotaviruses, noroviruses, sapoviruses, measles virus, Parvovirus, vaccinia virus, HTL virus, dengue virus, papilloma virus, molluscum virus, rabies virus, JC virus, arbovirus, encephalitis viruses, hantavirus and the like. Viruses involved in microbial infectious diseases are suitably herpes simplex virus type 1 or type 2.

In the present invention, examples of bacteria involved in microbial infectious diseases include *Vibrio cholerae, Salmonella bacteria, Escherichia coli, Legionella bacteria, Bacillus anthracia, Helicobacter pylori, Listeria monocytogenes*, tubercle bacilli, non-tuberculous acid-fast bacteria, staphylococci, streptococci, pneumococci, *Neisseria meningitidis*, pneumobacilli, *Serratia* bacteria, *Corynebacterium diphtheriae*, brucellae, *Bartonella henselae, Erysipelothrix rhusiopathiae*, actinomycetes, Lyme disease *Borrelia, Clostridium perfringens*, dysentery bacilli, *Yersinia pestis, Clostridium tetani, Enterobacter* bacteria and the like.

In the present invention, examples of fungi involved in microbial infectious diseases include *Candida, Aspergillus, Cryptococcus, Blastomyces, Coccidioides, Histoplasma, Paracoccidioides, Sporothrix* and the like.

In the present invention, examples of protozoans involved in microbial infectious diseases include malaria protozoans, toxoplasma protozoans and the like.

In the present invention, examples of parasites involved in microbial infectious diseases include dysenteric ameba, ascarids, *Babesia, Cryptosporidium, Giardia lamblia*, uncinaria, oxyuris, schistosomes, taeniid, trichinae, *trichuris* and the like.

In the present invention, examples of other microorganisms involved in microbial infectious diseases include mycoplasmata, spirochete and the like.

In the present invention, an activator of cytotoxic T cells comprising an EP4 agonist (hereinafter sometimes abbreviated an agent of the present invention) can also be used in combination with an antigen peptide(s) as a sensitizer or adjuvant thereof. It is preferable that the antigen peptide(s) used be an antigen that allows CTLs to specifically recognize the cancer or microorganism targeted for immunopotentiation by an agent of the present invention. For example, with the expectation for potentiation of immunity against melanomas, TRP-2 (Tyrosinase-related protein 2), a kind of melanoma-specific antigen peptide, may be used as the antigen peptide.

Examples of other antigen peptides include cancer (tumor) antigen peptides, virus antigen peptides and the like. Examples of cancer (tumor) antigen peptides include MAGE-1, MAGE-2, MAGE-3, MAGE-A4, MAGE-6, MART1, TRP-1, tyrosinase, gp100, HER2/neu, CEA, β-catenin, CHP, CpG, MUC-1, NY-ESO-1, BAGE, GAGE-1, GAGE-2, SAGE, LAGE, WT-1, hTERT, CDK4, p15, p53, PSA, gp1001, MAGE-12, telomerase, SART, SYT-SSX, survivin, CTL precursor-oriented peptide, MN/CA9, OY-TES-1, SCP-1, GnT-V, PRAME and the like. Examples of virus antigen peptides include EB virus antigens, cytomegalovirus antigens, herpes virus antigens (e.g., HSV glycoprotein B), influenza virus antigens, HIV antigens and the like. Examples of still other antigen peptides include *Salmonella* antigens, dysentery antigens, *Enterobacter* antigens, protozoa- or parasite-derived antigens and the like.

As is obvious to those skilled in the art, the aforementioned cancer (tumor) antigen peptides can be used as appropriate according to the cancer being the target of treatment and the particular major histocompatibility antigen to which the antigen peptides bind (Human Leukocyte Antigen; HLA). For example, when a melanoma is the target, an antigen peptide(s) that binds to HLA-A0201 or HLA-A2402 may be used; specifically, it is preferable that MART-1, gp-100, MAGE-2, MAGE-3, tyrosinase, or TRP-2 be used.

Likewise, for virus antigen peptides, when a herpes virus infection is the target, it is preferable that HSV glycoprotein B be used.

Also, as is obvious to those skilled in the art, the aforementioned antigen peptides are preferably have partial sequences corresponding to epitopes specifically recognized by CTLs. For example, in the case of TRP-2, VYDFFVWL (SEQ ID NO. 1) is used as a partial sequence thereof.

EP4 agonists used in the present invention include compounds that selectively bind to EP4 which is a subtype of prostaglandin E2 (PGE2) receptor and demonstrate agonist activity. Such EP4 agonists in the present invention do not only include ones which have ever been found but ones which will be found from now. EP4 agonists which have ever been found include, for example, the compounds described in the following (A)-(H) and (J)-(N) and the other EP4 agonist listed below.

(A) In the specification of JP2000-001472, it is described that the compound represented by the following formula (I) has EP4 agonistic activity. As well, the definition of each group of the compound represented by formula (I) is described in the specification of JP2000-001472 in detail. Accordingly, EP4 agonist used in the present invention includes the compound represented by formula (I)

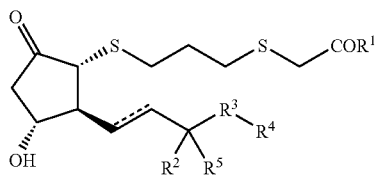

wherein $R^1$ is hydroxyl, C1-6 alkyloxy or $NR^6R^7$, wherein $R^6$ and $R^7$ are each independently hydrogen atom or C1-6 alkyl;
$R^2$ is hydrogen atom or hydroxyl;
$R^3$ is a bond or C1-6 alkylene;
$R^4$ is
(i) C1-8 alkyl, C2-8 alkenyl or C2-8 alkynyl substituted by 1 to 3 substituent(s) selected from C1-6 alkyloxy and halogen atom(s),
(ii) phenyloxy or C3-7 cycloalkyloxy,
(iii) furyl, furyloxy, thienyl, thienyloxy, naphthyl, naphthyloxy, phthalanyl or phthalanyloxy,
(iv) phenyl, phenyloxy, C3-7 cycloalkyl or C3-7 cycloalkyloxy substituted by 1 to 3 substituent(s) selected from the following groups:
(1) C1-6 alkyl, (2) C2-6 alkenyl, (3) C2-6 alkynyl, (4) C1-6 alkyloxy, (5) C1-6 alkyloxy-C1-6 alkyl, (6) C1-6 alkyloxy-C1-6 alkyloxy, (7) C2-6 alkenyloxy-C1-6 alkyl, (8) C1-6 alkyl substituted by 1 to 3 hydroxy, (9) C1-6 alkyl substituted by 1 to 3 halogen atom(s), (10) C1-6 alkylthio, (11) C1-6 alkylthio-C1-6 alkyl, (12) C1-6 alkylthio-C1-6 alkyloxy, (13) C2-6 alkenylthio-C1-6 alkyl, (14) C1-6 alkylsulfonyl, (15) halogen atom, (16) trihalomethyl, (17) cyano, (18) nitro, (19) amino, (20) hydroxy, (21) C3-7 cycloalkyl, (22) C3-7 cycloalkyloxy, (23) C3-7 cycloalkyl-C1-6 alkyl, (24) C3-7 cycloalkyloxy-C1-6 alkyl, (25) phenyl, (26) phenyloxy, (27) phenyl-C1-6 alkyl, (28) phenyl-C2-6 alkenyl, (29) phenyl-C2-6 alkynyl, (30) phenyloxy-C1-6 alkyl, (31) phenyloxy-C2-6 alkenyl, (32) phenyloxy-C2-6 alkynyl, (33) furyl, (34) furyloxy, (35) furyl-C1-6 alkyl, (36) furyloxy-C1-6 alkyl, (37) thienyl, (38) thienyloxy, (39) thienyl-C1-6 alkyl or (40) thienyloxy-C1-6 alkyl, wherein the above mentioned phenyl, furyl, thienyl and cycloalkyl are optionally substituted by 1 to 3 substituent(s) selected from C1-6 alkyl, C1-6 alkyloxy, C1-6 alkyloxy-C1-6 alkyl, nitro, halogen, trihalomethyl, amino and hydroxyl;
or
(v) furyl, furyloxy, thienyl, thienyloxy, naphthyl, naphthyloxy, phthalanyl or phthalanyloxy substituted by 1 to 3 substituent(s) selected from the following groups:
(1) C1-6 alkyl, (2) C2-6 alkenyl, (3) C2-6 alkynyl, (4) C1-6 alkyloxy, (5) C1-6 alkyloxy-C1-6 alkyl, (6) C1-6 alkyloxy-C1-6 alkyloxy, (7) C2-6 alkenyloxy-C1-6 alkyl, (8) C1-6 alkyl substituted by 1 to 3 hydroxy, (9) C1-6 alkyl substituted by 1 to 3 halogen atom(s), (10) C1-6 alkylthio, (11) C1-6 alkylthio-C1-6 alkyl, (12) C1-6 alkylthio-C1-6 alkyloxy, (13) C2-6 alkenylthio-C1-6 alkyl, (14) C1-6 alkylsulfonyl, (15) halogen atom, (16) trihalomethyl, (17) cyano, (18) nitro, (19) amino, (20) hydroxy, (21) C3-7 cycloalkyl, (22) C3-7 cycloalkyloxy, (23) C3-7 cycloalkyl-C1-6 alkyl, (24) C3-7 cycloalkyloxy-C1-6 alkyl, (25) phenyl, (26) phenyloxy, (27) phenyl-C1-6 alkyl, (28) phenyl-C2-6 alkenyl, (29) phenyl-C2-6 alkynyl, (30) phenyloxy-C1-6 alkyl, (31) phenyloxy-C2-6 alkenyl, (32) phenyloxy-C2-6 alkynyl, (33) furyl, (34) furyloxy, (35) furyl-C1-6 alkyl, (36) furyloxy-C1-6 alkyl, (37) thienyl, (38) thienyloxy, (39) thienyl-C1-6 alkyl or (40) thienyloxy-C1-6 alkyl, wherein the above mentioned phenyl, furyl, thienyl and cycloalkyl being optionally substituted by 1 to 3 substituent(s) selected from C1-6 alkyl, C1-6 alkyloxy, C1-6 alkyloxy-C1-6 alkyl, nitro, halogen, trihalomethyl, amino and hydroxyl;
$R^5$ is hydrogen atom or C1-6 alkyl;

⌇ is double bond or single bond,
with the proviso that $R^2$ is hydrogen atom, C1-6 alkylene represented by $R^3$ may be substituted by one hydroxy, a mixture of 8-epi compound which is an equilibrium compound thereof, a non toxic salt thereof or a cyclodextrin clathrate thereof.

In addition, the configuration of the 8th position in the above compound is shown as α-configuration, but as is clear to the person skilled in the art, the 8α-compounds are in equilibrium with the 8β-compounds, that is 8-epi compounds. Therefore, the compounds of the formula (I) include mixtures of 8α-compounds and isomeric 8β-compounds.

(B) In the pamphlet of WO02/042268, it is described that the compound represented by the following formula (IB) has EP4 agonistic activity. As well, the definition of each group of the compound represented by formula (IB) is described in the pamphlet of WO02/042268 in detail. Accordingly, EP4 agonist used in the present invention includes the compound represented by formula (IB)

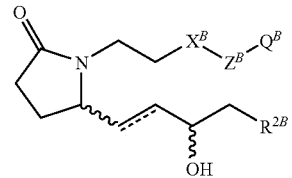

wherein the dotted line is a bond or no bond,
$X^B$ is —$CH_2$— or —O—,
$Z^B$ is —$(CH_2)_3$—, thienyl, thiazolyl or phenyl, provided that $X^B$ is O, then $Z^B$ is phenyl,
$Q^B$ is carboxy, C1-4 alkoxycarbonyl or tetrazolyl,
$R^{2B}$ is —$Ar^B$ or —$Ar^{1B}$—$V^B$—$Ar^{2B}$—,
$V^B$ is a bond, —O—, —$OCH_2$— or —$CH_2O$—,
$Ar^B$ is partially saturated, fully saturated or fully unsaturated 5 to 8 membered ring optionally having 1 to 4 heteroatoms selected voluntarily from oxygen, sulfur and nitrogen, or bicyclic ring consisting of two fused partially saturated, fully saturated or fully unsaturated 5 to 6 membered rings, optionally having 1 to 4 heteroatoms selected voluntarily from oxygen, sulfur and oxygen, said partially or fully saturated ring or bicyclic ring optionally having 1 or 2 oxo groups substituted on carbon or 1 or 2 oxo groups substituted on sulfur,
$Ar^{1B}$ and $Ar^{2B}$ are each independently a partially saturated, fully saturated or fully unsaturated 5 to 8 membered ring optionally having 1 to 4 heteroatoms selected voluntarily from oxygen, sulfur or nitrogen, said partially or fully saturated ring optionally having one or two oxo groups substituted on carbon or 1 or 2 oxo groups substituted on sulfur,
said $Ar^B$ moiety is optionally substituted on carbon or nitrogen, on one ring if the moiety is monocyclic, or one or both rings if the moiety is bicyclic, with up to three substituents selected from the following (1)-(29); (1) hydroxy, (2) halogen atom, (3) carboxy, (4) C1-7 alkoxy, (5) C1-4 alkoxy C1-4 alkyl, (6) C1-7 alkyl, (7) C2-7 alkenyl, (8) C3-7 cycloalkyl, (9) C3-7 cycloalkyl C1-4 alkyl, (10) C3-7 cycloalkyl C1-4 alkanoyl, (11) formyl, (12) C1-8 alkanoyl, (13) C1-6 alkanoyl C1-4 alkyl, (14) C1-4 alkanoylamino, (15) C1-4 alkoxycarbonylamino, (16) hydroxysulfonyl, (17) aminocarbonylamino or mono-N-, di-N,N-, di-N,N'-, or tri-N,N,N'-aminocarbonyl substituted C1-4 alkyl, (18) sulfonamide, (19) C1-4 alkylsulfonamide, (20) amino, (21) mono-N— or di-N,N—C1-4 alkylamino, (22) carbamoyl, (23) mono-N— or di-N,N—C1-4 alkylcarbamoyl, (24) cyano, (25) thiol, (26) C1-6 alkylthio, (27) C1-6 alkylsulfinyl, (28) C1-4 alkylsulfonyl, (29) mono-N— or di-N,N—C1-4 alkylaminosulfinyl, wherein said alkyl and alkoxy substituents in the definition of $Ar^B$ are optionally substituted on carbon with up to three fluorine atom, said $Ar^{1B}$ and $Ar^{2B}$ moieties are optionally substituted on carbon or nitrogen with up to three substituents selected from the following (1)-(29); (1) hydroxy, (2) halogen atom, (3) carboxy, (4) C1-7 alkoxy, (5) C1-4 alkoxy C1-4 alkyl, (6) C1-7 alkyl, (7) C2-7 alkenyl, (8) C3-7 cycloalkyl, (9) C3-7 cycloalkyl C1-4 alkyl, (10) C3-7 cycloalkyl C1-4 alkanoyl, (11) formyl, (12) C1-8 alkanoyl, (13) C1-6 alkanoyl C1-4 alkyl, (14) C1-4 alkanoylamino, (15) C1-4 alkoxycarbonylamino, (16) hydroxysulfonyl, (17) aminocarbonylamino or mono-N-, di-N,N-, di-N,N'-, or tri-N,N,N'-aminocarbonyl substituted C1-4 alkyl, (18) sulfonamide, (19) C1-4 alkylsulfonamide, (20) amino, (21) mono-N— or di-N,N—C1-4 alkylamino, (22) carbamoyl, (23) mono-N— or di-N,N—C1-4 alkylcarbamoyl, (24) cyano, (25) thiol, (26) C1-6 alkylthio, (27) C1-6 alkylsulfinyl, (28) C1-4 alkylsulfonyl, (29) mono-N— or di-N,N—C1-4 alkylaminosulfinyl, wherein said alkyl and alkoxy substituents in the definition of $Ar^{1B}$ and $Ar^{2B}$ are optionally substituted on carbon with up to three fluorine atom, provided that (a) when $X^B$ is —(CH$_2$)— and $Z^B$ is —(CH$_2$)$_3$—, then $R^{2B}$ is not thienyl, phenyl or phenyl monosubstituted with chlorine, fluorine, phenyl, methoxy, trifluoromethoxy or C1-4 alkyl, (b) when $X^B$ is —(CH$_2$)—, $Z^B$ is —(CH$_2$)$_3$—, and $Q^B$ is carboxy or C1-4 alkoxycarbonyl, then $R^{2B}$ is not (i) C5-7 cycloalkyl or (ii) phenyl, thienyl or furyl each of which may be optionally monosubstituted or disubstituted by one or two substituents selected from (1) halogen atom or (2) C1-3 alkyl which may be substituted by one or more halogen atoms or C1-4 alkoxy, a salt thereof, an N-oxide thereof or a solvate thereof, or a prodrug thereof, or a cyclodextrin clathrate thereof.

(C) In the pamphlet of WO03/008377, it is described that the compound represented by the following formula (IC) has EP4 agonistic activity. As well, the definition of each group of the compound represented by formula (IC) is described in the pamphlet of WO03/008377 in detail. Accordingly, EP4 agonist of the present invention includes the compound represented by formula (IC)

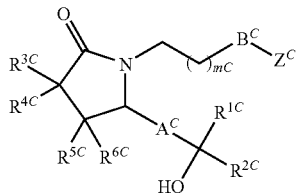

(IC)

wherein $A^C$ is —CH$_2$—CH$_2$— or —CH=CH—,
$B^C$ is single bond, aryl or heteroaryl,
$Z^C$ is —C(O)OR$^{\prime C}$, —C(O)NR$^{\prime L}$R$^{\prime\prime C}$, —C(O)NSO$_2$R$^{\prime C}$, —PR$^{\prime C}$(O)(OR$^{\prime C}$), —PO(OR$^{\prime C}$)$_2$ or tetrazol-5-yl (wherein, R$^{\prime C}$ and R$^{\prime\prime C}$ are each independently hydrogen atom or C1-6 alkyl),
mC is 1, 2, 3, 4, 5 or 6,
$R^{1C}$ is alkyl, alkenyl, alkynyl, cycloalkylalkyl, heterocyclylalkyl, aryl, arylalkyl, heteroaryl, when $B^C$ is aryl or heteroaryl and $R^{3C}$, $R^{4C}$, $R^{5C}$ and $R^{6C}$ are not simultaneously hydrogen atom, or $R^{1C}$ is heterocyclylalkyl, aryl, arylalkyl, heteroaryl, when $B^C$ is single bond and $R^{1C}$, $R^{5C}$ and $R^{6C}$ are simultaneously hydrogen atom,
$R^{2C}$ is hydrogen atom, C1-6 alkyl, C1-6 alkenyl or C1-6 alkynyl,
$R^{3C}$, $R^{4C}$, $R^{5C}$ and $R^{6C}$ are each independently hydrogen atom or C1-6 alkyl, $R^{3C}$ and $R^{4C}$, $R^{5C}$ and $R^{6C}$ or $R^{3C}$ and $R^{5C}$ taken together with the atom to which they are attached may form C3-7 alkyl ring,
a salt thereof, an N-oxide thereof or a solvate thereof, or a prodrug thereof, or a cyclodextrin clathrate thereof.

(D) In the pamphlet of WO03/035064, it is described that the compound represented by the following formula (ID) binds to EP4. As well, the definition of each group of the compound represented by formula (ID) is described in the pamphlet of WO03/035064 in detail. Accordingly, EP$_4$ agonist used in the present invention includes the compound represented by formula (ID)

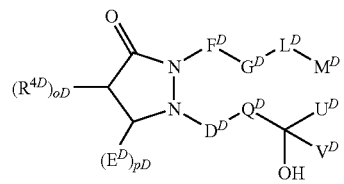

(ID)

wherein each $R^{4D}$ is independently hydrogen atom, optionally substituted aryl, optionally substituted carbocyclic aryl or optionally substituted heteroaromatic,
$E^D$ is hydrogen atom, hydroxyl, optionally substituted alkoxy or optionally substituted alkylthio,
oD and pD are each independently 0, 1 or 2, the sum of oD and pD is at least 1,
$F^D$ is —(CH$_2$)$_{nD}$ (wherein nD is an integer of from 1 to 6),
$G^D$ is —C≡C—, —CH=CH—, —CH$_2$—, optionally substituted carbocyclic aryl or optionally substituted heteroaromatic,
$L^D$ is (CH$_2$)$_{n'D}$ (wherein n'D is an integer of from 0 to 3),
$M^D$ is COX$^D$, SO$_2$X$^D$ (wherein X$^D$ is OR$^{\prime D}$ or NHR$^{\prime D}$, R$^{\prime D}$ is H or optionally substituted alkyl), optionally substituted tetrazol, NO$_2$, NHSO$_2$R$^D$ or NHC(O)R$^D$, wherein R$^D$ is H, optionally substituted alkyl,
$D^D$ is (CH$_2$)$_{n''D}$ (wherein n''D is an integer of from 0 to 2),
$Q^D$ is (CH$_2$)$_{N'''D}$ (wherein n'''D is 0 or 1), —CH=CH— or optionally substituted carbocyclic aryl, preferably optionally substituted phenyl,
$U^D$ and $V^D$ are each independently optionally substituted alkyl, optionally substituted alkenyl, optionally substituted alkynyl, optionally substituted carbocyclic aryl, or optionally substituted heteroaromatic,
provided that, the compound wherein G$^D$ is CH$_2$, n$^D$ is 3, E$^D$ is hydrogen atom and pD is 2, R4$^D$ is hydrogen atom and oD is 2, n''D is 2, n'''D is 0, V$^D$ is alkyl, is excepted,
a salt thereof, an N-oxide thereof or a solvate thereof, a prodrug thereof, or a cyclodextrin clathrate thereof.

(E) In the pamphlet of WO03/053923, it is described that the compound represented by the following formula (IE) binds to EP4. As well, the definition of each group of the compound represented by formula (IE) is described in the pamphlet of WO03/053923 in detail. Accordingly, EP4 agonist used in the present invention includes the compound represented by formula (IE)

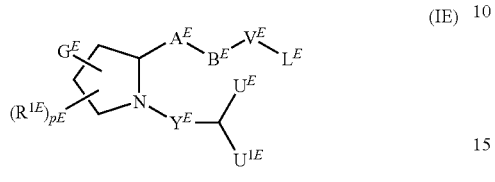

wherein, $R^{1E}$ is each independently hydrogen atom, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclic aryl, optionally substituted aralkyl, optionally substituted heteroalicyclic, optionally substituted heteroaryl, optionally substituted heteroarylalkyl or optionally substituted heteroalicyclicalkyl, $G^E$ is oxo, halogen atom, optionally substituted alkyl, optionally substituted alkoxy, hydroxyl, carboxylate, optionally substituted alkylcarboxylate ester, $P^E$ is an integer of from 0 to 4, $Y^E$ is $(CR^{2E}R^{3E})_{qE}$ which may include 0 or 1 C=C double bond, wherein qE is an integer of from 1 to 6, $R^{2E}$ and $R^{3E}$ are each independently hydrogen atom, optionally substituted alkyl, optionally substituted alkenyl, optionally substituted alkynyl, hydroxyl, halogen atom or optionally substituted alkoxy, $U^E$ and $U^{1E}$ are each independently hydrogen atom, hydroxyl or optionally substituted alkyl, $A^E$ is O, S, $(CR^{2E}R^{3E})_{q'E}$ (wherein, q'E is an integer of from 1 to 6), $B^E$ is $(CR^{2E}R^{3E})_{nE}$ or single bond, $A^E$ and $B^E$ take together to form an optionally substituted 1,2-vinylene or ethynylene, $V^E$ is $(CR^{2E}R^{3E})_{mE}$, optionally substituted divalent aryl or optionally substituted divalent heteroaryl, $L^E$ is $C(O)Z^E$, $Z^E$ is hydroxyl, optionally substituted alkyl, optionally substituted alkenyl, optionally substituted alkynyl, optionally substituted heteroalkyl, optionally substituted heteroalkenyl, optionally substituted heteroalkynyl, amino, $NR^{4E}R^{5E}$, optionally substituted cycloalkyl, optionally substituted heterocycloalkyl, optionally substituted carbocyclic aryl, optionally substituted heteroaryl, optionally substituted arylalkyl or optionally substituted heteroarylalkyl, nE is an integer of from 0 to 3, mE is an integer of from 1 to 6, $R^{4E}$ and $R^{5E}$ are each independently hydrogen atom, optionally substituted alkyl, optionally substituted cycloalkyl, optionally substituted heterocycloalkyl, optionally substituted alkenyl, optionally substituted alkynyl, optionally substituted heteroalkyl, optionally substituted heteroalkenyl, optionally substituted heteroalkynyl, optionally substituted carbocyclic aryl, optionally substituted heteroaryl, optionally substituted arylalkl or optionally substituted heteroarylalkl, or $R^{4E}$ and $R^{5E}$ take together to be heterocycloalkyl, a salt thereof, an N-oxide thereof or a solvate thereof, or a prodrug thereof, or a cylcodextrin clathrate thereof.

(F) In the pamphlet of WO03/103664, it is described that the compound represented by the following formula (IF) has EP4 agonistic activity. As well, the definition of each group of the compound represented by formula (IF) is described in the pamphlet of WO03/103664 in detail. Accordingly, EP4 agonist used in the present invention includes the compound represented by formula (IF)

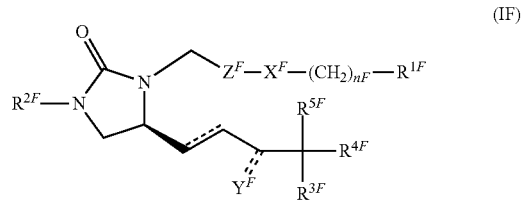

wherein $X^F$ is single bond, oxygen atom or sulfur atom, $Y^F$ is =O or —OH, $R^{1F}$ is hydroxyl, CN, $(CH_2)_{pF}CO_2R^{6F}$, $(CH_2)_{nF}SO_3R^{6F}$, —$CF_2SO_2NH_2$, —$SO_2NH_2$, —$CHNHSO_2R^{2F}$—, —$SO_2NHCOR^{6F}$, —$PO(OH)_2$, $CONHPO_2R^{6F}$, $CONHR^{8F}$, C1-4 alkoxy, —$(CH_2)_{nF}NR^{6F}R^{7F}$, hydroxymethylketone or —$(CH_2)_{nF}$ heterocyclyl, said heterocyclyl unsubstituted or substituted with 1 to 3 $R^{aF}$ and optionally containing an acidic hydrogen atom, $R^{2F}$ is hydrogen atom, C6-10 aryl or C1-4 alkyl, $R^{3F}$ and $R^{4F}$ are each independently hydrogen atom, halogen atom or C1-6 alkyl, $R^{5F}$ is $(CH_2)_{mF}$C6-10aryl, $(CH_2)_{mF}$C5-10heteroaryl, $(CH_2)_{mF}$C3-10heterocycloalkyl or $(CH_2)_{mF}$C3-10 cycloalkyl, said cycloalkyl, heterocycloalkyl, aryl or heteroaryl unsubstituted or substituted with 1 to 3 $R^{aF}$, $R^{6F}$ and $R^{7F}$ are hydrogen atom or C1-4 alkyl, $R^{8F}$ is hydrogen atom or sulfonyl, $Z^F$ is $(C(R^{bF})_2)_{nF}$,

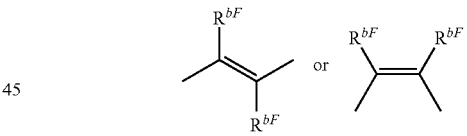

$R^{bF}$ is independently hydrogen atom, halogen atom, C1-6 alkyl or C3-6 cycloalkyl, $R^{aF}$ is C1-6 alkoxy, C1-6 alkyl, $CF_3$, nitro, amino, cyano, C1-6 alkylamino or halogen atom, ===== is double bond or single bond, pF is 1 to 3, nF is 0 to 4, mF is 0 to 8, a salt thereof, an N-oxide thereof or a solvate thereof, or a prodrug thereof, or a cyclodextrin clathrate thereof.

(G) In the pamphlet of US2005/0049227, it is described that the compound represented by the following formula (IG) has EP4 agonistic activity. As well, the definition of each group of the compound represented by formula (IG) is described in the pamphlet of US2005/0049227 in detail. Accordingly, EP4 agonist used in the present invention includes the compound represented by formula (IG)

(IG)

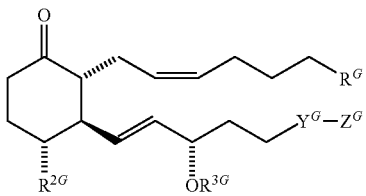

wherein $R^G$ is $CO_2R^{4G}$, $CONR^{4G}_2$, $CH_2OR^{4G}$, $CONR^{4G}SO_2R^{4G}$, $P(O)(OR^{4G})$,

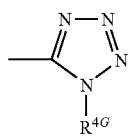

$R^{4G}$ is hydrogen atom, phenyl, C1-6 alkyl,
$R^{1G}$ and $R^{2G}$ are each independently hydrogen atom, hydroxyl, C1-6 alkyloxy, C1-6 acyloxy,
$R^{3G}$ is hydrogen atom, C1-6 alkyl, C1-6 acyl,
$Y^G$ is bond, or —$CH_2$—, —O—, —S—, —N—,
$Z^G$ is C3-10 alkyl, C3-10 cycloalkyl, 6 to 10 membered aromatic carbocyclic ring, 4 to 10 membered aromatic heterocyclic ring containing one hetero atom selected from nitrogen atom, oxygen atom and sulfur atom,
a salt thereof, an N-oxide thereof or a solvate thereof, or a prodrug thereof, or a cyclodextrin clathrate thereof.

(H) In the pamphlet of WO2004/085430, it is described that the compound represented by the following formula (IH) has EP4 agonistic activity. As well, the definition of each group of the compound represented by formula (IH) is described in the pamphlet of WO2004/085430 in detail. Accordingly, EP4 agonist used in the present invention includes the compound represented by formula (IH)

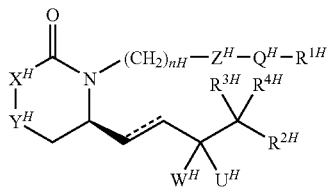

wherein $Q^H$ is $(CH_2)_{mH}$, $(CH_2)_{mH}$—C6-10 aryl, $(CH_2)_{mH}$—C5-10 heterocyclic ring, $(CH_2)_{mH}$—C3-10 heterocyclic alkyl, $(CH_2)_{mH}$—C3-8 cycloalkyl, methylene substituted by two halogen atoms, said cycloalkyl, heterocyclic alkyl, aryl, or heterocyclic ring may be substituted by three $R_{aH}$,
$X^H$ and $Y^H$ are each independently methylene, oxygen atom, nitrogen atom substituted by $R^{9H}$, sulfur atom, provided that, $X^H$ and $Y^H$ are not oxygen atom, nitrogen atom substituted by $R^{9H}$, or sulfur atom at the same time,
$U^H$ is hydrogen atom, C1-3 alkyl, or is not present when $W^H$ is oxo,
$W^H$ is hydroxyl, oxo, provided that $U^T$ is not present when $W^H$ is oxo,
$R^{1H}$ is —$(CH_2)_{pH}$-hydroxyl, —$(CH_2)_{pH}$-cyano, —$(CH_2)_{pH}$—$CO_2R^{10H}$, —$(CH_2)_{nH}$—$SO_3R^{6H}$, —$(CH_2)_{pH}$—$CF_2SO_2NH_2$, —$(CH_2)_{pH}$—$SO_2NH_2$, —$(CH_2)_{pH}$—$CONHSO_2R^{2H}$, —$(CH_2)_{pH}$—$SO_2NHCOR^{2H}$, —$(CH_2)_{pH}$—$PO(OH)_2$, $(CH_2)_{pH}$—$CONHPO_2R^{6H}$, —$(CH_2)_{pH}$—$CONHR^{8H}$, —$(CH_2)_{pH}$—C1-4 alkoxy, —$(CH_2)_{pH}$-cycloalkyl, —$(CH_2)_{pH}$-hydroxymethylketone, —$(CH_2)_{nH}$-heterocyclic ring, said heterocyclic ring optionally is substituted by 1 to 3 $R^{aH}$ and optionally contains an acidic hydroxyl,
$R^{2H}$ is independently C1-10 alkyl, $(CH_2)_{mH}$—C6-10 aryl, $(CH_2)_{mH}$-O5-10 heterocyclic ring, $(CH_2)_{mH}$—C3-10 heterocyclic alkyl, $(CH_2)_{mH}$—C3-8 cycloalkyl, O—C1-10 alkyl, O—C6-10 aryl, O—C3-10 cycloalkyl, O—C3-10 heterocyclic alkyl, provided that $R^{2H}$ is O—C1-10 alkyl, O—C6-10 aryl, O—C3-10 cycloalkyl, O—C3-10 heterocyclic alkyl, then $R^{3H}$ and $R^{4H}$ are not halogen atoms, said alkyl, cycloalkyl, heterocyclic alkyl, aryl, or heterocyclic ring optionally substituted by 1 to 3 $R^{aH}$,
$R^{3H}$ and $R^{4H}$ are each independently hydrogen atom, halogen atom, C1-6 alkyl, or $R^{3H}$ and $R^{4H}$ may be taken together to form a 3-7 membered carbocyclic ring optionally containing of 1 to 2 hetero atoms selected from oxygen atom, sulfur atom, SO, $SO_2$ and nitrogen atom substituted by $R^{9H}$
$R^{6H}$ and $R^{7H}$ are each independently hydrogen atom, C1-4 alkyl,
$R^{8H}$ is hydrogen atom, acyl, sulfonyl,
$R^{9H}$ is hydrogen atom, C1-6 alkyl, said alkyl optionally be substituted by 1 to 3 halogen atoms, cyano, hydroxyl, C1-6 alkoxy, C1-6 acyloxy, amino,
$R^{10H}$ is hydrogen atom, C1-10 alkyl, C3-10 cycloalkyl, $(CH_2)_{pH}$—C6-10 aryl, $(CH_2)_{pH}$—C5-10 heterocyclic ring, $CR^{6H}R^{7H}OC(O)$—C3-10 cycloalkyl, $CR^{6H}R^{7H}OC(O)$—C1-10 alkyl,
$Z^{TH}$ is triple bond, oxygen atom, sulfur atom, $(C(R^{bH})_2)_{nH}$, —CH═CH—,
$R^{bH}$ is hydrogen atom, C1-6 alkyl, halogen atom,
$R^{aH}$ is C1-6 alkoxy, C1-6 alkyl, $CF_3$, nitro, amino, cyano, C1-6 alkylamino, halogen atom, $R^{aH}$ is further aryl, heterocyclic ring, S—C1-6 alkyl, S—C6-10 aryl, S-O5-10 heterocyclic ring, $CO_2R^{6H}$, O—C6-10 aryl, 0-O5-10 heterocyclic ring, $CH_2O$—C1-6 alkyl, $CH_2S$—C1-6 alkyl, $CH_2O$-aryl, $CH_2S$-aryl,
----- is double bond or single bond,
pH is 0 to 3,
nH is 0 to 4,
mH is 0 to 8,
a salt thereof, an N-oxide thereof or a solvate thereof, or a prodrug thereof, or a cyclodextrin clathrate thereof.

(J) In the pamphlet of WO2004/085431, it is described that the compound represented by the following formula (IJ) has $EP_4$ agonistic activity. As well, the definition of each group of the compound represented by formula (IJ) is described in the pamphlet of WO2004/085431 in detail. Accordingly, $EP_4$ agonist used in the present invention includes the compound represented by formula (IJ)

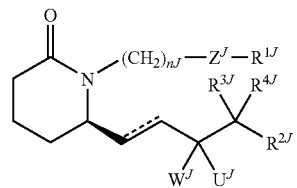

wherein $U^J$ is hydrogen atom, C1-3 alkyl, or is not present when $W^J$ is oxo, $W^J$ is hydroxyl, oxo, provided that, $U^J$ is not present when $W^I$ is oxo, $Z^J$ is $(CH_2)_{nJ}$, —CH=CH—, $R^{1J}$ is $(CH_2)_{pJ}$-hydroxyl, $(CH_2)_{pJ}CO_2R^{10J}$, $(CH_2)_{nJ}$ heterocyclic ring, said heterocyclic ring is optionally substituted by 1 to 3 $R^{aJ}$ and optionally contains an acidic hydroxyl, $R^{2J}$ is independently C1-10 alkyl, $(CH_2)_{mJ}$—C6-10 aryl, $(CH_2)_{mJ}$C-5-10 heterocyclic ring, $(CH_2)_{mJ}$—C3-10 heterocyclic alkyl, $(CH_2)_{mJ}$—C3-8 cycloalkyl, said alkyl, cycloalkyl, heterocyclic alkyl, aryl, or heterocyclic ring may be substituted by 1 to 3 $R^{aJ}$, $R^{3J}$ and $R^{4J}$ are each independently hydrogen atom, halogen atom, C1-6 alkyl, $R^{6J}$ is hydrogen atom, C1-4 alkyl, $R^{10J}$ is hydrogen atom, C1-10 alkyl, C3-10 cycloalkyl, $(CH_2)_{pJ}$—C6-10 aryl, $(CH_2)_{pJ}$—C5-10 heterocyclic ring, $R^{aJ}$ is C1-6 alkoxy, C1-6 alkyl, $CF_3$, nitro, amino, cyano, C1-6 alkylamino, halogen atom, $R^{aJ}$ is further aryl, heterocyclic ring, S—C1-6 alkyl, S—C6-10 aryl, S-O5-10 heterocyclic ring, O—C6-10 aryl, O—C5-10 heterocyclic ring, $CO_2R^{6J}$, $CH_2O$—C1-6 alkyl, $CH_2S$—C1-6 alkyl, $CH_2O$-aryl, $CH_2S$-aryl, ═══ is double bond or single bond, pJ is 0 to 3, nJ is 0 to 4, mJ is 0 to 8, a salt thereof, an N-oxide thereof or a solvate thereof, or a prodrug thereof, or a cyclodextrin clathrate thereof.

(K) In the pamphlet of WO2004/063158, it is described that the compound represented by the following formula (IK) has $EP_4$ agonistic activity. As well, the definition of each group of the compound represented by formula (IK) is described in the pamphlet of WO2004/063158 in detail. Accordingly, $EP_4$ agonist used in the present invention includes the compound represented by formula (IK)

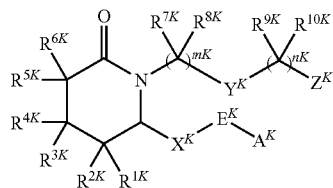

wherein mK is 1 to 4, nK is 0 to 4, $A^K$ is alkyl, aryl, heteroaryl, arylalkyl, arylcycloalkyl, cycloalkylalkyl, aryloxyalkyl, $E^K$ is —CHOH—, —C(O)—, $X^K$ is —$(CH_2)_2$—, —CH=CH—, $Y^K$ is —$CH_2$—, —CH=CH—, arylene, heteroarylene, —O—, —S(O)$_{pK}$— (wherein pK is 0 to 2), —$NR^{aK}$— (wherein, $R^{aK}$ is hydrogen atom, alkyl), $Z^K$ is —$CH_2OH$—, —CHO, tetrazol-5-yl, —$COOR^{bK}$ (wherein $R^{bK}$ is hydrogen atom, alkyl), $R^{1K}$, $R^{2K}$, $R^{3K}$, $R^{4K}$, $R^{5K}$, $R^{6K}$, $R^{7K}$, $R^{8K}$, $R^{9K}$ and $R^{10K}$ are each independently hydrogen atom or alkyl, a salt thereof, an N-oxide thereof or a solvate thereof, or a prodrug thereof, or a cyclodextrin clathrate thereof.

(L) In the pamphlet of WO03/009872, it is described that the compound represented by the following formula (IL) has $EP_4$ agonistic activity. As well, the definition of each group of the compound represented by formula (IL) is described in the pamphlet of WO03/009872 in detail. Accordingly, $EP_4$ agonist used in the present invention includes the compound represented by formula (IL)

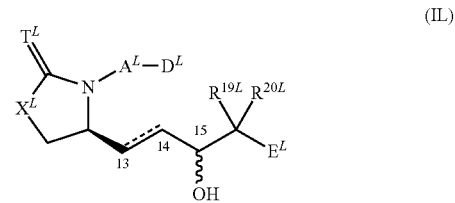

wherein ⌇ is (1) single bond or (2) double bond, $R^{19L}$ and $R^{20L}$ are each independently, (1) hydrogen atom, (2) C1-10 alkyl or (3) halogen atom, $T^L$ is (1) oxygen atom or (2) sulfur atom, $X^L$ is (1) —$CH_2$—, (2) —O— or (3) —S—, $A^L$ is $A^{1L}$ or $A^{2L}$, $A^{1L}$ is (1) C2-8 straight-chain alkylene optionally substituted by 1 to 2 C1-4 alkyl, (2) C2-8 straight-chain alkenylene optionally substituted by 1 to 2 C1-4 alkyl or (3) C2-8 straight-chain alkynylene optionally substituted by 1 to 2 C1-4 alkyl, $A^{2L}$ is -$G^{1L}$-$G^{2L}$-$G^{3L}$-, $G^{1L}$ is (1) C1-4 straight-chain alkylene optionally substituted by 1 to 2 C1-4 alkyl, (2) C2-4 straight-chain alkenylene optionally substituted by 1 to 2 C1-4 alkyl or (3) C2-4 straight-chain alkynylene optionally substituted by 1 to 2 C1-4 alkyl, $G^{2L}$ is (1) —$Y^L$—, (2) -(ring$1^L$)-, (3) —$Y^L$-(ring$1^L$)-, (4) -(ring$1^L$)-$Y^L$- or (5) —$Y^L$—(C1-4 alkylene)-(ring$1^L$)-, $Y^L$ is (1) —S—, (2) —SO—, (3) —$SO_2$—, (4) —O— or (5) —$NR^{1L}$—, $R^{1L}$ is (1) hydrogen atom, (2) C1-10 alkyl or (3) C2-10 acyl, $G^{3L}$ is (1) bond, (2) C1-4 straight-chain alkylene optionally substituted by 1 to 2 C1-4 alkyl, (3) C2-4 straight-chain alkenylene optionally substituted by 1 to 2 C1-4 alkyl or (4) C2-4 straight-chain alkynylene optionally substituted by 1 to 2 C1-4 alkyl, $D^L$ is $D^{1L}$ or $D^{2L}$, $D^{1L}$ is (1) —COON, (2) —$COOR^{2L}$, (3) tetrazol-5-yl or (4) $CONR^{3L}SO_2R^{4L}$, $R^{2L}$ is (1) C1-10 alkyl, (2) phenyl, (3) C1-10 alkyl substituted by phenyl or (4) biphenyl, $R^{3L}$ is (1) hydrogen atom or (2) C1-10 alkyl, $R^{4L}$ is (1) C1-10 alkyl or (2) phenyl, $D^{2L}$ is (1) —$CH_2OH$, (2) —$CH_2OR^{5L}$, (3) hydroxy, (4) —$OR^{5L}$, (5) formyl, (6) —$CONR^{6L}R^{7L}$, (7) —$CONR^{6L}SO_2R^{8L}$, (8) —CO—(NH-amino acid residue-CO)$_{mL}$—OH, (9) —O—(CO— amino acid residue — NH)$_{mL}$—H, (10) —$COOR^{9L}$, (11) —OCO—$R^{10L}$, (12) —COO—$Z^{1L}$—$Z^{2L}$—$Z^{3L}$, (13)

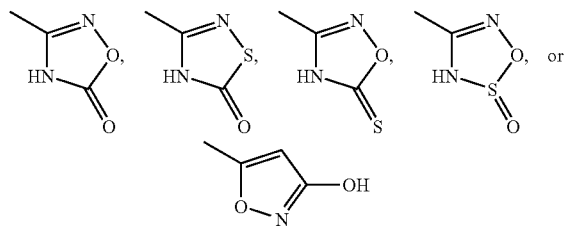

$R^{5L}$ is C1-10 alkyl, $R^{6L}$ and $R^{7L}$ are each independently, (1) hydrogen atom or (2) C1-10 alkyl, $R^{8L}$ is C1-10 alkyl substituted by phenyl, $R^{9L}$ is (1) C1-10 alkyl substituted by biphenyl optionally substituted by 1 to 3 C1-10 alkyl, C1-10 alkoxy or halogen atom or (2) biphenyl substituted by 1 to 3 C1-10 alkyl, C1-10 alkoxy or halogen atom(s), $R^{10L}$ is (1) phenyl or (2) C1-10 alkyl, mL is 1 or 2, $Z^{1L}$ is (1) C1-15 alkylene, (2) C2-15 alkenylene or (3) C2-15 alkynylene, $Z^{2L}$ is (1) —CO—, (2) —OCO—, (3) —COO—, (4) —$CONR^{11L}$—, (5) —NR$^{12L}$CO—, (6) —O—, (7) —S—, (8) —SO—, (9) —SO$_2$—, (10) —NR$^{13L}$—, (11) —NR$^{14L}$CONR$^{15L}$—, (12) —NR$^{16L}$COO—, (13) —OCONR$^{17L}$— or (14) —OCOO—, Z$^{3L}$ is (1) hydrogen atom, (2) C1-15 alkyl, (3) C2-15 alkenyl, (4) C2-15 alkynyl, (5) ring2$^L$ or (6) C1-10 alkyl substituted by C1-10 alkoxy, C1-10 alkylthio, C1-10 alkyl-NR$^{18L}$— or ring2$^L$, R$^{11L}$, R$^{12L}$, R$^{13L}$, R$^{14L}$, R$^{15L}$, R$^{16L}$, R$^{17L}$ and R$^{18L}$ are each independently (1) hydrogen atom or (2) C1-15 alkyl, R$^{11L}$ and Z$^{3L}$ may be taken together with the nitrogen atom to which they are attached to form 5 to 7 membered saturated mono-heterocyclic ring, and the heterocyclic ring may contain another one hetero atom selected from oxygen, nitrogen and sulfur atom, E$^L$ is E$^{1L}$ or E$^{2L}$, E$^{1L}$ is (1) C3-7 cycloalkyl or (2) ring3$^L$, E$^{2L}$ is (1) C3-7 cycloalkyl, (2) ring4$^L$ or (3) ring5$^L$, ring1$^L$ and ring5$^L$ are optionally substituted by 1 to 3 R$^{21L}$ and/or R$^{22L}$, ring3$^L$ is optionally substituted by 1 to 2 R$^{21L}$, C3-7 cycloalkyl represented by E$^{2L}$ is substituted by one of R$^{21L}$ or R$^{22L}$, and optionally substituted by other 1 to 2 R$^{21L}$ and/or R$^{22L}$, ring4$^L$ is substituted by one of R$^{22L}$, optionally substituted by other 1 to 2 R$^{21L}$ and/or R$^{22L}$, and heterocyclic ring formed by R$^{11L}$, Z$^{3L}$ and the nitrogen to which Z$^{3L}$ is attached or ring2$^L$ may be substituted by R$^{23L}$, R$^{21L}$ is (1) C1-10 alkyl, (2) C1-10 alkoxy, (3) halogen atom, (4) nitro, (5) C1-10 alkyl substituted by 1 to 3 halogen atom(s) or (6) phenyl, R$^{22L}$ is (1) C2-10 alkenyl, (2) C2-10 alkynyl, (3) C1-10 alkylthio, (4) hydroxy, (5) —NR$^{24L}$R$^{25L}$, (6) C1-10 alkyl substituted by C1-10 alkoxy, (7) C1-10 alkyl substituted by C1-10 alkoxy substituted by 1 to 3 halogen atom(s), (8) C1-10 alkyl substituted by —NR$^{24L}$R$^{25L}$, (9) ring6$^L$, (10) —O-ring7$^L$, (11) C1-10 alkyl substituted by ring7$^L$, (12) C2-10 alkenyl substituted by ring7$^L$, (13) C2-10 alkynyl substituted by ring7$^L$, (14) C1-10 alkoxy substituted by ring7$^L$, (15) C1-10 alkyl substituted by —O-ring7$^L$, (16) —COOR$^{26L}$ or (17) C1-10 alkoxy substituted by 1 to 3 halogen atom(s), R$^{24L}$, R$^{25L}$ and R$^{26L}$ are each independently, (1) hydrogen atom or (2) C1-10 alkyl, R$^{23L}$ is (1) C1-15 alkyl, (2) C2-15 alkenyl, (3) C2-15 alkynyl or (4) C1-10 alkyl substituted by C1-10 alkoxy, C1-10 alkylthio or C1-10 alkyl-NR$^{27L}$—, R$^{27L}$ is (1) hydrogen atom or (2) C1-10 alkyl, ring1$^L$, ring2$^L$, ring5$^L$, ring6$^L$ and ring7$^L$ are (1) C3-15 mono-, bi- or tri-carbocyclic aryl which may be partially or fully saturated or (2) 3 to 15 membered mono-, bi- or tri-heterocyclic aryl containing 1 to 4 hetero atom(s) selected from oxygen, nitrogen and sulfur atom(s) which may be partially or fully saturated, ring3$^L$ and ring4$^L$ are (1) thienyl, (2) phenyl or (3) furyl, ring6$^L$ and ring7$^L$ may be substituted by 1 to 3 R$^{28L}$, R$^{28L}$ is (1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1 to 3 halogen atom(s) or (9) C1-10 alkyl substituted by C1-10 alkoxy substituted by 1 to 3 halogen atom(s);

a salt thereof, an N-oxide thereof or a solvate thereof, or a prodrug thereof, or a cyclodextrin clathrate thereof, Among the compound represented by formula (IL), a compound represented by formula (IL-1)

wherein E$^{1-1}$ has the same meaning as E$^L$, R$^{L-1}$ is hydrogen atom or C1-4 alkyl, is preferred.

(M) In the pamphlet of WO00/003980, it is described that the compound represented by the following formula (IM) has EP$_4$ agonistic activity. As well, the definition of each group of the compound represented by formula (IM) is described in the pamphlet of WO00/003980 in detail. Accordingly, EP$_4$ agonist used in the present invention includes the compound represented by formula (IM)

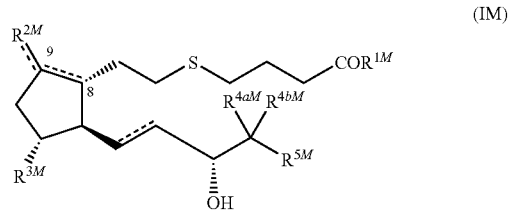

wherein R$^{1M}$ is hydroxy, C1-6 alkyloxy or NR$^{6M}$R$^{7M}$, wherein R$^{6M}$ and R$^{7B}$ are each independently hydrogen or C1-4 alkyl, R$^{2M}$ is oxygen atom, halogen atom or O—COR$^{8M}$, wherein R$^{8M}$ is C1-4 alkyl, phenyl or phenyl (C1-4 alkyl)), R$^{3M}$ is hydrogen atom or hydroxy, R$^{4aM}$ and R$^{4bM}$ are each independently hydrogen atom or C1-4 alkyl, R$^{5M}$ is phenyl substituted with the following substituent(s):

i) 1 to 3 selected from (a) C1-4 alkyloxy-C1-4 alkyl, (b) C2-4 alkenyloxy-C1-4 alkyl, (c) C2-4 alkynyloxy-C1-4 alkyl, (d) C3-7 cycloalkyloxy-C1-4 alkyl, (e) C3-7 cycloalkyl(C1-4 alkyloxy)-C1-4 alkyl, (f) phenyloxy-C1-4 alkyl, (g) phenyl-C1-4 alkyloxy-C1-4 alkyl, (h) C1-4 alkylthio-C1-4 alkyl, (i) C2-4 alkenylthio-C1-4 alkyl, (j) C2-4 alkynylthio-C1-4 alkyl, (k) C3-7 cycloalkylthio-C1-4 alkyl, (l) C3-7 cycloalkyl(C1-4 alkylthio)-C1-4 alkyl, (m) phenylthio-C1-4alkyl and (n) phenyl-C1-4 alkylthio-C1-4 alkyl, ii) (a) C1-4 alkyloxy-C1-4 alkyl and C1-4 alkyl, (b) C1-4 alkyloxy-C1-4 alkyl and C1-4 alkyloxy, (c) C1-4 alkyloxy-C1-4 alkyl and hydroxy, (d) C1-4 alkyloxy-C1-4 alkyl and halogen atom, (e) C1-4 alkylthio-C1-4 alkyl and C1-4 alkyl, (f) C1-4 alkylthio-C1-4 alkyl and C1-4 alkyloxy, (g) C1-4 alkylthio-C1-4 alkyl and hydroxy or (h) C1-4 alkylthio-C1-4 alkyl and halogen atom, iii) (a) haloalkyl or (b) hydroxy-C1-4 alkyl, or iv) C1-4 alkyl and hydroxy;

⟍⟋ is single bond or double bond, and it is not double bond continuously, with the proviso that when R$^{2M}$ is O—COR$^{8M}$, the 8-9 position represents double bond, a salt thereof, an N-oxide thereof or a solvate thereof, or a prodrug thereof, or a cyclodextrin clathrate thereof.

(N) In the pamphlet of WO03/007941, it is described that the compound represented by the following formula (IN) has EP$_4$ agonistic activity. As well, the definition of each group of the compound represented by formula (IN) is described in the pamphlet of WO03/007941 in detail. Accordingly, EP$_4$ agonist used in the present invention includes the compound represented by formula (IN)

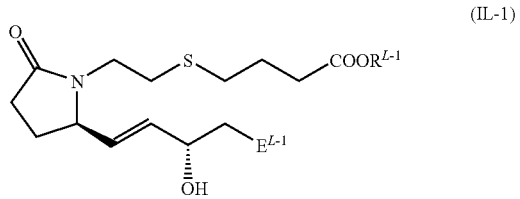

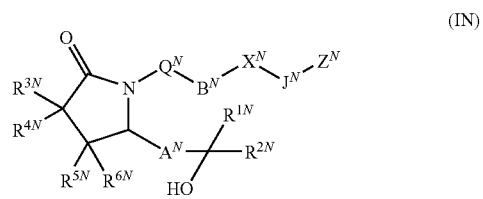

wherein $Q^N$ is $CH_2$ or oxygen atom, $B^N$ is —$CH_2$—, —$(CH_2)_2$—, —$(CH_2)_3$—, —$(CH_2)_4$—, —$(CH_2)_5$—, —CH=CH—, —$CH_2$—CH=CH—, —CH=CH—$CH_2$— or —$CH_2$—CH=CH—$CH_2$—, provided that when $B^N$ is —CH=CH—, or —CH=CH—$CH_2$—, then $Q^N$ is $CH_2$, $X^N$ is —$NR^{aN}$—, wherein $R^{aN}$ is hydrogen atom, halogen atom, C1-6 alkyl, C1-6 acyl, —O—, —S—, —SO—, —$SO_2$— or single bond, provided that $X^N$ is single bond, then $Q^N$ is oxygen atom, $J^N$ is —$(CR^{bN}R^{cN})_{nN}$—, wherein nN is an integer of from 1 to 4, $R^{bN}$ and $R^{cN}$ are both hydrogen atom, or one or two of $R^{bN}$ and $R^{cN}$ are lower alkyl and the remainder is hydrogen atom, or $R^{bN}$ and $R^{cN}$ if attached to the same carbon atom form a C2-5 polymethylene, or —$CH_2$—CH=CH—, $A^N$ is —$CH_2$—$CH_2$—, —CH=CH— or —C≡C—, $Z^N$ is $CH_2OH$, —$C(O)OR^{tN}$, —$C(O)NR^{tN}R^{mN}$, —$C(O)NSO_2R^{tN}$, —$P(C1-6\ alkyl)(O)(OR^{tN})$, —$PO(OR^{tN})_2$ or tetrazol-5-yl, wherein $R^{tN}$ and $R^{mN}$ are each independently hydrogen atom or C1-6 alkyl, nN is 1, 2, 3 or 4, $R^{1N}$ is —$(CH_2)_{pN}R^{7N}$ or —$(CH_2)_{qN}OR^{8N}$, wherein $R^{7N}$ and $R^{8N}$ are each independently C1-6 alkyl, halo C1-6 alkyl, C3-6 cycloalkyl, heterocyclyl, aryl or heteroaryl, pN and qN are each independently 0, 1, 2, 3, 4 or 5, $R^{2N}$ is hydrogen atom, C1-6 alkyl, C1-6 alkenyl, C1-6 alkynyl, $R^{3N}$, $R^{4N}$, $R^{5N}$ and $R^{6N}$ are each independently hydrogen atom or C1-6 alkyl, a salt thereof, an N-oxide thereof or a solvate thereof, or a prodrug thereof, or a cyclodextrin clathrate thereof.

As the other EP4 agonists, the compounds described in the pamphlets of WO2005/012232, WO2005/023267, WO2005/100339, WO2005/116010, WO2006/014206, WO2006/014207, WO2006/058063, WO2006/055481, WO2006/052630, WO2006/52892, WO2006/080323, US2006/252742, WO2006/113571, WO2006/137472, WO2007/014454, WO2007/014462, WO2007/088190, WO2007/143825, WO2008/012344 and WO2008/012347 are included.

As EP$_4$ agonist of the present invention, the compound represented by formula (I), (IL), (IL-1), (IM) or (IN) is preferred. More preferably, the compounds of 11α,15α,-dihydroxy-9-oxo-16-(3-methoxymethylphenyl)-17,18,19,20-tetranor-3,7-dithiaprost-13E-enoic acid, 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[24(1R,2R,3R)-3-hydroxy-2-{(1E,3S)-3-hydroxy-4-[3-(methoxymethyl)phenyl]but-1-enyl}-5-oxocyclopentyl) ethyl]sulfanyl}butanoic acid, methyl 4-{[2-((1R,2R,3R)-3-hydroxy-2-{(1E,3S)-3-hydroxy-4-[3-(methoxymethyl) phenyl]but-1-enyl}-5-oxocyclopentyl)ethyl] sulfanyl}butanoate etc. are included. Further preferably, the compounds of 4-[(2-{(2R)-2-[(1E,3S)-4-(4-fluorophenyl)-3-hydroxybut-1-enyl]-5-oxopyrrolidine-1-yl}ethyl)sulfanyl] butanoic acid, 4-{[24(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid, methyl 4-{[2-((1R,2R,3R)-3-hydroxy-2-{(1E,3S)-3-hydroxy-4-[3-(methoxymethyl)phenyl]but-1-enyl}-5-oxocyclopentyl) ethyl]sulfanyl}butanoate are included.

[Isomers]

Unless otherwise specified, all isomers are included in the above each compound represented by formulae (I), (IB) to (IH) and (IJ) to (IN) (hereinafter collectively abbreviated to the compound used in the present invention). For example, alkyl, alkenyl, alkynyl, alkyloxy, alkoxy, alkenyloxy, alkynyloxy, alkylthio, alkylsulfinyl, alkylsulfonyl, alkylene, alkenylene, alkynylene, acyl and acyloxy group means straight-chain or branched-chain ones. In addition, isomers on double bond, ring, fused ring (E-, Z-, cis-, trans-isomer), isomers generated from asymmetric carbon atom(s) (R-, S-isomer, α-, β-configuration, enantiomer, diastereomer), optically active isomers (D-, L-, d-, l-isomer), polar compounds generated by chromatographic separation (more polar compound, less polar compound), equilibrium compounds, rotational isomers, mixtures thereof at voluntary ratios and racemic mixtures are also included in the present invention. Moreover, tautomers are included.

[Salts and Solvates]

The salts of the compound used in the present invention include pharmaceutically acceptable salts. As pharmaceutically acceptable salts, non-toxic, water-soluble salts are preferred. As appropriate salts, for example, salts of alkali metals (e.g., potassium, sodium, lithium, etc.), salts of alkaline earth metals (e.g., calcium, magnesium, etc.), ammonium salts (e.g., tetramethylammonium salt, tetrabutylammonium salt, etc.), salts of organic amine (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts (salts of inorganic acids (e.g., hydrochloride, hydrobromide, hydroiodide, sulfate, phosphate, nitrate etc.), and salts of organic acids (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate etc.) are included.

Moreover, the salt includes a quaternary ammonium salt. The quaternary ammonium salt is the compound where nitrogen of the compound used in the present invention is quarternalized by $R^o$. $R^o$ is C1-8 alkyl optionally substituted by phenyl.

A solvate of the compound used in the present invention includes the solvate of, such as, water, alcohol solvent (e.g., methanol, ethanol etc.) and so on. The solvate is preferably non-toxic and water-soluble. The suitable solvate includes, for example, solvate of water or alcohol (e.g., ethanol etc.). Moreover, the solvate of the compound used in the present invention includes a solvate of the alkali (earth) metal salt, the ammonium salt, the organic amine salt and the acid addition salt of the compound used in the prevention invention.

The compounds used in the present invention can be converted into salts thereof and solvates thereof by known methods.

[Cyclodextrin Clathrate Compounds]

The compounds used in the present invention may be converted into the corresponding cyclodextrin clathrates by the method described in the specification of JP-B-50-3362, 52-31404 or 61-52146 using α-, β- or γ-cyclodextrin or a mixture thereof. Converting into the corresponding cyclodextrin clathrates serves to increase the stability and solubility in water of the compounds, and therefore it is useful in the use for pharmaceuticals. Among the cyclodextrin clathrate compound, it is preferable to convert into α-cyclodextrin clathrate compound.

[Prodrugs]

The prodrug of the compounds used in the present invention means a compound is converted into the compound used in the present invention by reaction with enzymes, gastric acids and so on within an organism. The prodrug of the compounds used in the present invention include, when the compounds used in the present invention have amino, the prodrug is the compound the amino of which is acylated, alkylated, or phosphorylated (e.g., the compound is that the amino of the compound used in the present invention is eicosanoated, alanylated, pentylaminocarbonylated, (5-methyl-2-oxo-1,3-dioxolan-4-yl)methoxycarbonylated, tetrahydrofuranated, pyrrolidylmethylated, pivaloyloxymethylated, acetoxymethylated, tert-butylated, etc.); when the compounds used in the present invention have hydroxy, the prodrug is the compound the hydroxy of which is acylated, alkylated, phosphorylated or borated (e.g., the compound is that the hydroxy of the compound used in the present invention is acetylated, palmitoylated, propanoylated, pivaloylated, succinylated, fumarylated, alanylated, dimethylaminomethylcarbonylated etc.); when the compounds used in the present invention have carboxy, the prodrug is the compound the carboxyl of which is esterified or amidated (e.g., the compound is that the carboxy of the compound used in the present invention is ethylesterified, phenylesterified, carboxymethylesterified, dimethylaminomethylesterified, pivaloyloxymethylesterified, 1-{(ethoxycarbonyl)oxy}ethylesterified, phthalidylesterified, (5-methyl-2-oxo-1,3-dioxolen-4-yl)methylesterified, 1-{[(cyclohexyloxy)carbonyl]oxy}ethylesterified, methylamidated etc.); and so on. These compounds can be prepared by known methods. In addition, the prodrug of the compound used in the present invention may be either hydrate or non-hydrate. In addition, the prodrug of the compounds used in present invention may be converted into the compound of the present invention under the physiological condition which is described in "the development of medicine" vol. 7 "molecular design" published in 1991 Hirokawa shoten p.p. 163-198. Further, the compounds used in present invention may be labeled with isotopes (e.g. $^3H$, $^{14}C$ $^{35}S$, $^{125}I$ etc.) and so on.

[Processes for the Preparation of the Compound in the Present Invention]

EP4 agonists used in the present invention can be prepared by known methods, such as, the methods described in JP2000-001472, WO02/042268, WO2003/008377, WO2003/035064, WO2003/053923, WO2003/103664, WO2003/007941, US2005/0049227, WO2004/085430, WO2004/085431, WO2004/063158, WO2003/009872, WO00/03980, WO2003/007941, WO2005/012232, WO2005/023267, WO2005/100339, WO2005/116010, WO2006/014206, WO2006/014207, WO2006/058063, WO2006/055481, WO2006/052630, WO2006/52892, WO2006/080323, US2006/252742, WO2006/113571, WO2006/137472, WO2007/014454, WO2007/014462, WO2007/088190, WO2007/143825, WO2008/012344, WO2008/012347 etc, or the pursuant methods thereof. For example, 11α,15α,-dihydroxy-9-oxo-16-(3-methoxymethylphenyl)-17,18,19,20-tetranor-3,7-dithiaprost-13E-enoic acid, which is exemplified as the preferred EP4 agonist, can be prepared by the method described in JP2000-001472. 4-[(2-{(2R)-2-[(1E,3S)-4-(4-fluorophenyl)-3-hydroxybut-1-enyl]-5-oxopyrrolidine-1-yl}ethyl)sulfanyl]butanoic acid can be prepared by the method described in WO2003/009872. 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid and methyl 4-{[24 (1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate can be prepared by the method described in WO00/03980.

[Toxicity]

Toxicity of EP4 agonists used in the present invention is very low, and it is safe enough to use as a pharmaceutical agent.

[Application to Pharmaceutical Products]

EP4 agonists exhibit an immunopotentiating activity through the activation of a cytotoxic T cell, and is therefore useful for the prevention and/or treatment of cancer or a microorganism-mediated infection disease in mammal such as human or animal aside from human, for example monkey, sheep, cattle, horse, dog, cat, rabbit, rat, mouse etc. The EP4 agonist can be used as the sensitizer or an adjuvant when using it together with the above antigen peptides.

EP4 agonists used in the present invention may be administered in combination with other medicaments besides the above-mentioned antigen peptide as a concomitant medication to accomplish the following purposes:
1) To compensate for and/or enhance treatment effect of activation of cytotoxic T cell;
2) To improve the kinetics/absorption of the compound to be combined and reduce the dose of said $EP_4$ agonist; and/or
3) To eliminate the adverse effect of said $EP_4$ agonist to be combined EP4 agonists used in the present invention and the antigen peptides and/or other medicaments may be administered in the form of formulation having these components incorporated in one preparation or may be administered in separate preparations. In the case where these medicaments are administered in separate preparations, they may be administered simultaneously or at different times. In the latter case, EP4 agonists, the antigen peptides and other medicaments may be administrated in any order.

The other medicaments may be low-molecular compounds. In addition, they may be macromolecular protein, polypeptide, polynucleotide (DNA, RNA, and gene), antisense, decoy, antibody or vaccine and so on, with the proviso that the above antigen peptide is excluded. The dose of the antigen peptide and/or the other medicaments can be accordingly selected as a standard of clinical dose. Additionally, the compounding ratio of EP4 agonists used in the present invention, the antigen peptides and/or the other medicaments can be accordingly selected by the age and body weight of administering object, the administration method, the administration time etc. For example, the anitigenic peptide and/or the other medicaments may be used from 0.01 to 100 parts by weight relative to 1 part by weight of EP4 agonist used in the present invention. The antigen peptide and/or the other medicaments may be administered combining arbitrary two kinds or more at appropriate ratio. The other medicaments to compensate for and/or enhance the effect of activation of cytotoxic T cell do not only include ones which have ever been found but ones which will be found from now based on the below-mentioned mechanism.

The other medicaments include immunostimulants, anticancer drugs such as alkylating agents, antimetabolites, anticancer antibodies, vegetable drugs, hormone drugs, platinum compounds, histone deacetylase (HDAC) inhibitors, poly (ADP-ribose)polymerase (PARP) inhibitors and so on, antiviral drugs, antibiotics, antifungal drugs, antiparasitics, antiprotozoal agents and the like.

The immunostimulants include, for example, lentinan, picibanil, krestin, sizofuran, ubenimex, interferon, lobenzarit, TF, GM-CSF, M-CSF, G-CSF, IL-1, IL-2, IL-3, IL-12 and the like.

The alkylating agents include, for example, nitrogen mustard N-oxide hydrochloride, cyclophosphamide, ifosfamide, melphalan, thiotepa, carboquone, busulfan, nimustine hydroxychloride, dacarbazine, ranimustine and the like.

The antimetabolites include, for example, methotrexate, mercaptopurine, 6-mercaptopurine riboside, fluorouracil, tegafur, tegafur/uracil, carmofur, doxifluridine, cytarabine, enocitabine, tegafur/gimestat/otastat, gemcitabine hydrochloride, cytarabine ocfosfate, procarbazine hydrochloride, hydroxycarbamide and the like.

The anticancer antibodies include, for example, actinomycin D, mitomycin C, daunorubicin hydrochloride, doxorubicin hydrochloride, aclarubicin hydrochloride, neocarzinostatin, pirarubicin hydrochloride, epirubicin (hydrochloride), idarubicin hydrochloride, chromomycin A3, bleomycin (hydrochloride), peplomycin sulfate, therarubicin, zinostatin stimalamer and the like.

The vegetable drugs include, for example, vinblastine sulfate, vincristine sulfate, vindesine sulfate, irinotecan hydrochloride, etoposide, flutamide, vinorelbine ditartrate, docetaxel hydrate, paclitaxel and the like.

The hormone drugs include, for example, estramustine phosphate sodium, mepitiostane, epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, exemestane and the like.

The platinum compounds include, for example, carboplatin, cisplatin, nedaplatin and the like.

The HDAC inhibitors include, for example, vorinostat, AN-9, belinostat, MGCD-0103, MS-275, panobinostat, romidepsin, tacedinaline, valproic acid, VP-101, CRA-024781, ITF-2357, pyroxamide, CS-055, EHT-0205, FR-135313, NSC-3852, PXD-118490, SAHA analog, LAQ-824 and the like.

The PARP inhibitors include, for example, GPI-15427, GPI-16539, GPI-18078, GPI-6000, GPI-6150, KU-0687, INO-1001, FK-866, 4-(4-(N,N-dimethylaminomethyl)phenyl)-5-hydroxyisoquinolinone, FR-255595, FR-257516, FR-261529, FR-247304, M-50916, ABT-472, ONO-1924H, DR-2313, CEP-8983, AG-014699, BGP-15, AAI-028, PD-141076, PD-141703, ONO-2231 and the like.

The antiviral drugs include, for example, anti HIV drugs such as CCR5 inhibitors, CXCR4 inhibitors, reverse transcriptase inhibitors, fusion inhibitors and so on, anti influenza viral drugs such as oseltamivir phosphate, zanamivir hydrate and so on, anti anti herpes drug such as acyclovir and so on, interferon-α or β, various immunoglobulin and the like.

The antibiotics include, for example, cefem antibiotics such as cefaclor and so on, penicillin antibiotic such as amoxicillin and so on, macrolide antibiotic such as erythromycin ethylsuccinate and so on, ceftibuten, sodium cefuroxime, doxorubicin, tobramycin, meropenem trihydrate, cefetamet pivoxil hydrochloride, astromicin sulfate, sisomicin sulfate, netilmicin sulfate and the like.

The antifungal drugs include, for example, itraconazole, fluconazole, lanoconazole, sulconazole nitrate, oxiconazole nitrate, econazole nitrate, itraconazole nitrate, croconazole hydrochloride nitrate, clotrimazole, terbinafine hydrochloride, tolnaftate, bifonazole, neticonazole hydrochloride, ketoconazole, butenafine hydrochloride, miconazole nitrate, voriconazole, amphotericin B, flucytosine, griseofulvin, micafungin and the like.

The antiparasitics include, for example, santonin, combantrin, supatonin, mebendazole, mintezol, eskazole, biltricide, quinine, fansidar, flagyl, haisigyn and the like.

The antiprotozoal agents include, for example, metronidazol, pentamidine and the like.

In order to use EP4 agonist used in the present invention or EP4 agonist used in the present invention in combination with the antigen peptide and/or the other medicaments for the above purpose, these are normally administered to the entire or local part of human body orally or parenterally.

The doses to be administered are differently determined depending upon, for example, age, body weight, symptom, the desired therapeutic effect, the route of administration, and the duration of the treatment etc. In the human adult, the doses per person are generally from 0.1 ng to 1000 mg, by oral administration, from one time to several times per day, and from 0.1 ng to 1000 mg, by parenteral administration, from one time to several times per day, or continuous administration from 1 to 24 hours per day from vein or from 1 day to three month topically.

As mentioned above, the doses vary depending upon various conditions. Therefore, there are cases in which doses lower than the above described doses are enough or more administration is necessary greater doses than the ranges specified above.

EP4 agonist used in the present invention, or concomitant medication combined EP4 agonist used in the present invention with other preparations may be administered in the composition of, for example, solid compositions or liquid compositions, each for oral administration, or injections, external use, suppositories, eye drops or inhalant each for parenteral administration etc.

Examples of the solid preparations for internal use for oral administration include tablets, pills, capsules, powders, granules and the like. The capsules include hard capsules and soft capsules. The tablets include sublingual tablets, intraoral patches, orally fast disintegrating tablets and the like.

Such a solid preparation for internal use is prepared by a formulation method commonly employed by using one or more active substances either as it is or as a mixture with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer and a dissolution aid (glutamic acid, aspartic acid, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are involved in the scope thereof.

The sublingual tablets may be prepared or adjusted in accordance with a well known method. For example, a sublingual tablet is prepared by a formulation method commonly employed by using one or more active substances mixed with an excipient (lactose, mannitol, glucose, microcrystalline cellulose, colloidal silica, starch, etc.), a binder (hydroxypropylcellulose, polyvinylpyrrolidone, magnesium metasilicate aluminate, etc.), a disintegrator (starch, L-hydroxypropyl cellulose, carboxymethyl cellulose, croscarmellose sodium, calcium cellulose glycolate, etc.), a lubricant (magnesium stearate, etc.), a swelling agent (hydroxypropyl cellulose, hydroxylpropylmethy cellulose, carbopol, carboxymethyl cellulose, polyvinyl alcohol, xanthan gum, guar gum, etc.), a swelling aid agent (glucose, fructose, mannitol, xylitol, erythritol, maltose, trehalose, phosphate, citrate, silicate, glycine, glutamic acid, arginine, etc.), a stabilizer, a dissolution aid (polyethylene glycol, propylene glycol, glutamic acid, aspartic acid, etc.), a flavoring agent (orange, strawberry, mint, lemon, vanilla, etc.). If necessary, it may be coated with a coating agent (sucrose, gelatin, hydroxypropylcellulose, hydroxypropylmethylcellulose phthalate, etc.). If necessary, it may be coated with two or more layers. Moreover, it may also further comprise some additives such as antiseptics, antioxidants, coloring agents, sweetening agents and the like.

The intraoral patch may be prepared or adjusted in accordance with a well known method. For example, a intraoral patch is prepared by a formulation method commonly employed by using one or more active substances mixed with an excipient (lactose, mannitol, glucose, microcrystalline cellulose, colloidal silica, starch, etc.), a binder (hydroxypropylcellulose, polyvinylpyrrolidone, magnesium metasilicate aluminate, etc.), a disintegrator (starch, L-hydroxypropyl cellulose, carboxymethyl cellulose, croscarmellose sodium, calcium cellulose glycolate, etc.), a lubricant (magnesium stearate, etc.), a attach agent (hydroxypropyl cellulose, hydroxylpropylmethy cellulose, carbopol, carboxymethyl cellulose, polyvinyl alcohol, xanthan gum, guar gum, etc.), a attach aid agent (glucose, fructose, mannitol, xylitol, erythritol, maltose, trehalose, phosphate, citrate, silicate, glycine, glutamic acid, arginine, etc.), a stabilizer, a dissolution aid (polyethylene glycol, propylene glycol, glutamic acid, aspartic acid, etc.), a flavoring agent (orange, strawberry, mint, lemon, vanilla, etc.) and the like. If necessary, it may be coated with a coating agent (sucrose, gelatin, hydroxypropylcellulose, hydroxypropylmethylcellulose phthalate, etc.) and the like. If necessary, it may be coated with two or more layers. Moreover, it may also further comprise some additives such as antiseptics, antioxidants, coloring agents, sweetening agents and the like.

The orally fast disintegrating tablet may be prepared or adjusted in accordance with a well known method. For example, a orally fast disintegrating tablet is prepared by a formulation method commonly employed by using one or more active substances directly, or active substances by covering with adequate coating agent (ethylcellulose, hydroxypropylcellulose, hydroxypropylmethylcellulose, acrylic acid and methacrylic acid copolymer etc.), plasticizer (polyethylenegrycol, triethyl citrate etc.) to bulks or granulating bulk particles mixed with an excipient (lactose, mannitol, glucose, microcrystalline cellulose, colloidal silica, starch, etc.), a binder (hydroxypropylcellulose, polyvinylpyrrolidone, magnesium metasilicate aluminate, etc.), a disintegrator (starch, L-hydroxypropyl cellulose, carboxymethyl cellulose, croscarmellose sodium, calcium cellulose glycolate, etc.), a lubricant (magnesium stearate, etc.), a dispersion aid agent (glucose, fructose, mannitol, xylitol, erythritol, maltose, trehalose, phosphate, citrate, silicate, grylcine, glutamate, arginine etc.), a stabilizer and a dissolution aid (polyethylene glycol, propylene glycol, glutamic acid, aspartic acid, etc.), a flavoring agent (orange, strawberry, mint, lemon, vanilla, etc.) and the like. If necessary, it may be coated with a coating agent (sucrose, gelatin, hydroxypropylcellulose, hydroxypropylmethylcellulose phthalate, etc.) and the like. If necessary, it may be coated with two or more layers. Moreover, it may also further comprise some additives such as antiseptics, antioxidants, coloring agents, sweetening agents and the like.

Liquid forms for oral administration include pharmaceutically acceptable solutions, suspensions, emulsions, syrups and elixirs. In such forms, one or more of the active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

In the parenteral administration, formulation of external use include, for example, ointment, gel, cream, poultice, patch, liniment, atomized agent, inhalation, spray, eye drops, ear drops, and nasal spray, etc. They include one or more of the active compound(s) and be prepared or adjusted by known method or usual method.

Ointment is prepared by known method or usual method. For example, it is prepared or adjusted by levigation or fusion of one or more of the active compound(s) and substrate. The substrate of ointment is selected from known or usual one. For example, higher fatty acid or higher fatty acid ester (adipic acid, myristic acid, palmitic acid, stearic acid, oleic acid, adipic acid ester, myristic acid ester, palmitic acid ester, stearic acid ester, oleic acid ester, etc.), wax (yellow beeswax, spermaceti, ceresin, etc.), surfactant (polyoxyethylene alkyl ether phosphoric acid ester, etc.), higher alcohol (cetanol, stearil alcohol, cetostearyl alcohol, etc.), silicon oil (dimethyl polysiloxane, etc.), hydrocarbon (hydrophilic petrolatum, white petrolatum, purified lanolin, liquid paraffin, etc.), glycol (ethylene glycol, diethylene glycol, propylene glycol, polyethylene glycol, macrogol, etc.), vegetable oil (castor oil, olive oil, sesame oil, turpentine oil, etc.), animal oil (mink oil, egg yolk oil, squalane, squalene, etc.), water, absorption accelerator, skin fit inhibitor, etc. are used as single substance selected from them or mixture which consists of two or more kinds that is selected from them. Moreover, humectant, preservative agent, stabilizer, antioxidative agent, fragrant materials, etc. may be contained.

Gel is prepared by known method or usual method. For example, it is prepared or adjusted by fusion of one or more of the active compound(s) and substrate. The substrate of gel is selected from known or usual one. For example, lower alcohol (ethanol, isopropylalcohol, etc.), gelling agent (carboxy methyl cellulose, hydroxy ethyl cellulose, hydroxy propyl cellulose, ethyl cellulose, etc.), neutralizing agent (triethanolamine, diisopropanolamine, etc.), surfactant (polyethylene glycol monostearate, etc.), gum, water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Cream is prepared by known method or usual method. For example, it is prepared or adjusted by fusion or emulsification of one or more of the active compound(s) and substrate. The substrate of cream is selected from known or usual one. For example, higher fatty acid ester, lower alcohol, hydrocarbon, polyalcohol (propylene glycol, 1,3-butylene glycol, etc.), higher alcohol (2-hexyldecanol, cetanol, etc.), emulsifying agent (polyoxyethylene alkyl ether, fatty acid ester, etc.), water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Poultice is prepared by known method or usual method. For example, it is prepared by fusion of one or more of the active compound(s) and substrate, and then the kneaded one is laid over support medium. The substrate for poultice is selected from known or usual one. For example, thickening agent (polyacrylic acid, polyvinylpyrolidone, gum acacia, starch, gelatin, methyl cellulose, etc.), a wetting agent (urea, glycerin, propylenegrycol etc.), bulking agent (kaolin, zinc oxide, talc, calcium, magnesium, etc.), water, solubilizing agent, thickener, skin fit inhibitor, etc. are used as single substance selected from them or mixture which consists of two or more kinds that is selected from them. Moreover, preservative agent, antioxidative agent, fragrant materials, etc. may be contained.

Patch is prepared by known method or usual method. For example, it is prepared by fusion of one or more of the active compound(s) and substrate, and then laid over support medium. The substrate for patch is selected from known or usual one. For example, polymer substrate (styrene-isoprene-styrene block copolymer, polyisobutylene rubber, acrylic acid ester resin, acryl system copolymer resin, silicon rubber etc.), fat, higher fatty acid, percutaneous permeation accelerator (oleic acid, isopropyl myristate, D-menthol, crotamiton etc.), thickener (rosin derivative, alicyclic saturated hydrocarbon resin etc.), skin fit inhibitor (glycerin, crotamiton etc.), etc. are used as single substance selected from them or mixture which consists of two or more kinds that is selected from them. Moreover, preservative agent, antioxidative agent, fragrant materials, etc. may be contained. The patch includes, for example, a plaster agent such as a matrix (adhesive single layer) type, a reservoir type and the like, and a poultice etc. Further, in the matrix type, a drug dispersion type, a drug dissolution type and the like are included. The plaster agent is named tape agent.

Liniment is prepared by known method or usual method. For example, one or more of the active compound(s) may be dissolved, suspended or emulsified in water, alcohol (ethanol, polyethylene glycol, etc.), higher fatty acid, glycerin, soap, emulsifying agent, suspending agent, etc. as single substance selected from them or mixture which consists of two or more kinds that is selected from them. Moreover, preservative agent, antioxidative agent, fragrant materials, etc. may be contained.

Atomized agent, inhalation and spray may comprise in addition to a diluent, a stabilizer such as sodium bisulfite and an isotonization buffer such as sodium chloride, sodium citrate or citric acid. Moreover, aerosol is included.

The dosage of inhalations for parenreral administration include aerosol, powders for inhalation or liquids for inhalation. The liquids for inhalation may be dissolved or suspended in water or the other appropriate solvent as needed.

Such inhalations are prepared in a known method.

For example, a liquid for inhalation is prepared by selecting proper additives from an antiseptic (benzalkonium chloride or p-aminobenzonic acid), a coloring agent, a buffering agent (sodium phosphate or sodium acetate), an isotonizing agent (sodium chloride or concentrated glycerin), thickening agent (carboxyvinylpolymer), or an accelerator of absorption, etc., if necessary.

A powder for inhalation is prepared by selecting proper additives from a lubricant agent (such as stearin acid and the salt thereof), a binding agent, (such as starch, dextrin), a diluting agent (such as lactose, cellulose), a coloring agent, an antiseptic (such as benzalkonium chloride or p-aminobenzonic acid), an accelerator of absorption, etc., if necessary.

In case of administration of liquid for inhalation, spray (atomizer, nebulizer) is usually used and in case of administration of powder for inhalation, inhalation administration apparatus for powder agents is usually used.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof. Injections may comprise some additives, such as stabilizing agents, solution adjuvants (glutamic acid, aspartic acid, POLYSORBATE80 (registered trade mark) etc.), suspending agents, emulsifying agents, soothing agent, buffering agents, preservative. They may be sterilized at a final step, or may be prepared or adjusted by an aseptic manipulation. They may also be manufactured in the form of sterile solid forms, for example, freeze-dried products, which may be dissolved in sterile water or some other sterile diluent(s) for injection immediately before use.

The other compositions for parenteral administration include suppositories for intrarectal administration and vaginal suppositories for vaginal administration which comprise one or more of the active substance(s) and may be prepared by methods known per se.

To increase an effect of an agent of the present invention, particularly a potentiation of immunity against cancers, another therapeutic method for cancers may be used in combination with the agent. For example, other immunotherapies (e.g., transdermal immunotherapies (e.g., tape stripping method), NK (natural killer) cell therapy, CTL therapy (here, CTL therapy refers to an immunotherapy using extraneous cancer-specific CTLs in culture), cytokine therapy, CD3-LAK therapy, LAK therapy, dendritic cell vaccine therapy and the like), chemotherapy using the aforementioned anti-cancer agents, radiotherapy, particle ray (charged heavy particle ray) therapy, stereostatic radiation, thermotherapy, hematopoietic stem cell transplantation and the like can be mentioned. Preferably, a transdermal immunotherapy, particularly the tape stripping method, is used.

The tape stripping method specifically refers to a method for administering a substance that activates cytotoxic T cells (e.g., EP4 agonists, antigen peptides and the like used in an agent of the present invention) to a site from which the (skin epidermal) corneal layer has been physically or chemically removed, using a tape preparation with adhesive quality, acetone or the like, as described in Japanese Patent Publication No. 3879785 and elsewhere. Therein, it is preferable that a tape preparation with adhesive quality be used; specifically, preference is given to a tape preparation comprising an acrylic polymer, rubber-series polymer, hydrophilic polymer or the like used as an adhesive agent, and a plastic film (e.g., polyethylene, polyethylene terephthalate, polyurethane, polyethylene, polypropylene, polyester, polyvinyl acetate, ethylene-vinyl acetate copolymer and the like) used as a support. As a method of destroying the corneal layer using a tape preparation with adhesive quality, a method is available wherein the operation of adhering the tape preparation to the epidermal corneal layer surface and then peeling the preparation is repeated once to several times.

When an agent of the present invention is used in combination with the tape stripping method described above, the EP4 agonist used in the agent of the present invention may be administered in a state contained in the adhesive layer of the tape preparation used for the tape stripping method, or may be administered to a site from which the skin epidermal corneal layer or the corneal layer has been peeled by the tape stripping method, by an optionally chosen method (e.g., patch, injection), or may be administered anywhere other than the site (e.g., oral administration, intravenous administration, subcutaneous administration). Furthermore, when an antigen peptide(s) is concomitantly used, the antigen peptide(s) may be administered in a state contained in the adhesive layer of the tape preparation, or may be administered in a state contained in the adhesive layer together with an EP4 agonist, or may be administered to the above-described deprival site by an optionally chosen method (e.g., patch), or may be administered anywhere other than the site (e.g., intravenous administration).

In a method for administering the antigen peptide(s), the corneal layer is destroyed, after which the antigen peptide(s) solution of interest (dimethyl sulfoxide (DMSO), phosphate-buffered saline (PBS) and the like) is absorbed to a gauze pad of optionally chosen size, and the gauze is applied to one to several sites deprived of corneum. In administering the antigen peptide(s) to a plurality of portions, the antigen peptide(s) may be administered at different sites in the arms, femurs, abdomen and back. Regarding duration of administration, the antigen peptide(s) may be persistently administered for 1 to 3 months while the pad is replaced with a fresh supply every 24 hours.

To ensure that an effect of an agent of the present invention, particularly a potentiation of immunity against cancers, especially against melanomas, is efficiently manifested, it is preferable that the EP4 agonists, antigen peptides, other therapeutic methods for cancers and the like mentioned above be combined as shown below. Specifically, it is preferable that any one of 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid, and methyl 4-{[24(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate, as an EP4 agonist(s), and an antigen peptide(s) be used in combination; more preferably, any one of 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid, and methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate, an antigen peptide(s), and transdermal immunotherapy as another cancer therapeutic method are combined; still more preferably, any one of 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[24(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid, and methyl 4-{[24(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate, a melanoma-specific antigen peptide (TRP-2) as an antigen peptide, and the tape stripping method are combined.

The aforementioned combinations can be used as pharmaceuticals or pharmaceutical compositions in immunotherapies for melanomas using the tape stripping method. In a preferred embodiment thereof, for example, to a site from which the skin epidermal corneal layer or the corneal layer has been peeled by the tape stripping method, any one of the EP4 agonists 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[24(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid, and methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate, contained as an active ingredient in an adhesive layer, is administered in the form of a patch. Furthermore, when using the patch, it is preferable to use the antigen peptide TRP-2 in combination therewith; in this embodiment, it is more preferable that the TRP-2 and the EP4 agonist be administered in separate patches, or administered in a single patch whose adhesive layer contains both TRP-2 and any one of 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[24(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid, and methyl 4-{[24(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate.

In the above-described pharmaceuticals or pharmaceutical compositions (particularly patches), it is possible to prevent the drug from entering the systemic circulation by topical administration to the skin, and hence to minimize adverse effects that are possibly caused by the entry thereof in the systemic circulation due to oral administration, intravenous administration and the like.

The present invention also encompasses cytotoxic T cells activated by an EP4 agonist. The cells can be produced by treating immature T cells cultured by a publicly known technique with an optimal amount of the EP4 agonist. Whether the cytotoxic T cells have been activated can be determined by a method in common use, e.g., flowcytometric analysis and the like. The cells thus obtained can be used for immunotherapies, e.g., CTL therapy.

EXAMPLES

The fact that EP4 agonists have an effect of the present invention was demonstrated by the experiments described below. The experimental procedures used are shown below, which, however, are not to be construed as limiting the scope of the present invention. For example, by following the same procedures, but using the antigen peptides listed above in place of the peptide antigens TRP-2 and HSVgpB, which were used in Examples below, the actions to potentiate immunity against target cancers and microbial infectious diseases can also be evaluated.

Biological Examples

Example 1

Activation of Cytotoxic T Cells in Cervical Lymph Nodes

Example 1(1)

The corneal layers of the auricles of C57BL/6(B6) mice were destroyed by repeating a stripping procedure using an adhesive tape in 10 cycles, and an antigen peptide or EP4 agonist was applied as a test substance. The antigen peptide used was a melanoma-specific antigen peptide (Accord K.K. Peptide Business Department; hereinafter abbreviated TRP-2) in solution in 70% ethanol; 10 μg was applied to one side of each auricle. The EP4 agonist used was 11α,15α,-dihydroxy-9-oxo-16-(3-methoxymethylphenyl)-17,18,19,20-tetranol-3,7-dithiaprost-13E-enoic acid (hereinafter abbreviated Compound A-(1)) in solution in a mixed solvent of acetone: olive oil=10:1; 20 μL of 100 μM solution was applied to one side of each auricle. One week after application of the test substance, the cervical lymph nodes were removed. The frequency of TRP-2-specific CTLs was determined relative to the total number of mononucleocytes in the cervical lymph nodes as 100 by a flowcytometric analysis (FACScaliber; Becton, Dickinson and Company.) with a tetramer (Medical & Biological Laboratories Co., Ltd.). Four experimental groups were established: (1) a group undergoing tape stripping (hereinafter abbreviated TS) alone, (2) a group undergoing TS followed by application of TRP-2, (3) a group undergoing TS followed by application of Compound A-(1), and (4) a group undergoing TS followed by application of TRP-2 and Compound A-(1).

Note that the melanoma-specific antigen peptide TRP-2 was synthesized on the basis of a partial sequence described in the aforementioned Non-patent Document 1 (SEQ ID NO. 1) (Accord K.K. Peptide Business Department).

TRP-2; tyrosinase-related protein 2 181-188.

Example 1(2)

The same procedures as Example 1(1) were followed except that the EP4 agonists used were 4-[(2-{(2R)-2-[(1E, 3S)-4-(4-fluorophenyl)-3-hydroxybut-1-enyl]-5-oxopyrrolidin-1-yl}ethyl)sulfanyl]butanoic acid (hereinafter abbreviated Compound L-(1)) and 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid (hereinafter abbreviated Compound M-(1)); the action of each compound to activate cytotoxic T cells was evaluated. Four experimental groups were established: (1) a group undergoing TS alone, (2) a group undergoing TS followed by application of TRP-2, (3) a group undergoing TS followed by application of TRP-2 and Compound L-(1), and (4) a group undergoing TS followed by application of TRP-2 and Compound M-(1).

[Results]

The results of Example 1(1) and Example 1(2) are shown in Table 1 and Table 2, respectively, below.

TABLE 1

| Experimental group | (1) | (2) | (3) | (4) |
|---|---|---|---|---|
| Ratio of TRP-2-specific CTLs | 0.11 | 0.35 | 0.55 | 0.63 |

TABLE 2

| Experimental group | (1) | (2) | (3) | (4) |
|---|---|---|---|---|
| Ratio of TRP-2-specific CTLs | 1.19 | 1.28 | 1.92 | 1.66 |

These results show that in the group receiving Compound A-(1) applied as an EP4 agonist, compared with the group undergoing TS alone, the ratio of TRP-2-specific CTLs in cervical lymph nodes increased. Similar effects were observed with Compound L-(1) and Compound M-(1), suggesting that an EP4 agonist alone may exhibit an action to activate TRP-2-specific CTLs. The results from the experimental group (4) shown in Table 1 and those from the experimental groups (3) and (4) shown in Table 2 suggest that an EP4 agonist may have the action thereof enhanced when used in combination with an antigen peptide.

Example 1(3)

The same procedures as Example 1(1) were followed except that the antigen peptide used was the herpes simplex virus-specific antigen HSV glycoprotein B (hereinafter abbreviated HSVgpB), and that a flowcytometric analysis with a pentamer (ProImmune Company) was performed, and the action of each compound to activate cytotoxic T cells was evaluated. Five experimental groups were established: (1) a group undergoing TS alone, (2) a group undergoing TS followed by application of HSVgpB, (3) a group undergoing TS followed by application of HSVgpB and Compound A-(1), (4) a group undergoing TS followed by application of HSVgpB and Compound L-(1), and (5) a group undergoing TS followed by application of HSVgpB and Compound M-(1).

Note that the herpes simplex virus-specific antigen peptide HSVgpB was synthesized on the basis of the partial sequence shown by SEQ ID NO. 2 (Virology, Vol. 195, pp. 62-70, (1993)) (ProImmune Company).

HSVgpB; Herpes Simplex Virus glycoprotein B 498-505

[Results]

The results of Example 1(3) are shown in Table 3 below.

TABLE 3

| Experimental group | (1) | (2) | (3) | (4) | (5) |
|---|---|---|---|---|---|
| Ratio of HSVgpB-specific CTLs | 0.20 | 0.25 | 0.41 | 0.29 | 0.30 |

These results suggest that in addition to exhibiting an action to activate HSVgpB-specific CTLs, EP4 agonist may have the action thereof enhanced when used in combination with an antigen peptide.

Example 2

Activation of Cytotoxic T Cells in Isolated Langerhans Cells

A given area of an auricle epidermal sheet was removed from the corneal layer of one auricle of each C57BL/6(B6) mouse, and trypsinized to yield an epidermal cell suspension. The epidermal cell suspension obtained was subjected to panning using an antibody specific for I-A$^b$ antigen to isolate epidermal Langerhans cells. After each test substance (TRP-2 (concentration; 10 μg/mL) and Compound A-(1) (1 μM)) was added to the Langerhans cells isolated (cell density; $10^5$ cells per mL), the cells were cultured with a medium (cRPMI1640 medium; Sigma-Aldrich Japan). Half a day later, the cells were co-cultured with splenocytic lymphocytes isolated from B6 mouse cervical lymph nodes for 7 days. Subsequently, by a flowcytometric analysis (FACScaliber; Becton, Dickinson and Company.) using a tetramer (Medical & Biological Laboratories Co., Ltd.), the frequency of TRP-2-specific CTLs was determined relative to the total number of mononucleocytes in the medium as 100. Three experimental groups were established: (1) a group with no treatment, (2) a group with the addition of TRP-2, and (3) a group with the addition of both TRP-2 and Compound A-(1).

[Results]

The results are shown in Table 4 below.

TABLE 4

| Experimental group | (1) | (2) | (3) |
|---|---|---|---|
| Ratio of TRP-2-specific CTLs | 2.1 | 3.2 | 6.6 |

In the group with the addition of TRP-2 as an antigen peptide (experimental group (2)), the ratio of TRP-2-specific CTLs in B6 splenocytic lymphocytes increased, demonstrating that TRP-2-specific CTLs were induced. This action was equivalent to that of Compound A-(1). Furthermore, the results from the group with the simultaneous addition of Compound A-(1) (experimental group (3)) suggested that irrespective of the presence or absence of TS, the potential for inducing TRP-2-specific CTLs may be enhanced by using an EP4 agonist and an antigen peptide in combination.

Example 3

Melanoma Growth Suppressing Action

The corneal layer was removed from the right auricle of each B6 mouse by TS in the same manner as Example 1, and test substances (TRP-2 and Compound A-(1)) were applied there; 2 weeks later, the left auricle was treated in the same manner. The test substances applied to both ears were used in the same combination; TRP-2 was applied at 10 μg for one side of each auricle, and Compound A-(1) was applied at 20 μl, of 100 μM solution for one side of each auricle. Four days after the above-described treatment, each mouse received $2 \times 10^5$ B16 melanoma cells (RIKEN's Cell Bank) by subcutaneous transplantation, and examined for tumor growth. Experimental groups were established as in Example 1(1) (5 animals in each group).

[Results]

Tumor diameter (mm), as an index of tumor growth, was measured in each group at various days after inoculation of B16 melanoma cells; the results are shown in FIG. 1.

In the groups receiving Compound A-(1) applied as an EP4 agonist (experimental groups (3) and (4)), compared with the experimental group (1), the tumor diameter was smaller; decreased tumor growth rates were observed. Hence, it was suggested that an EP4 agonist alone may exhibit tumor growth suppressing action, and that this action may be equivalent to that of TRP-2, judging from a comparison with the experimental group (2). Furthermore, B16 melanoma cells did not take in any animals in the experimental group (4), suggesting that the combined effect of an EP4 agonist and antigen peptide suggested in Examples 1 and 2 may produce a potent enhancement of immunity against melanomas.

Example 4

Life-Prolonging Effect in Melanoma-Inoculated Mice $2 \times 10^5$ B16 melanoma cells were transplanted to B6 mice in the same manner as Example 3. On day 5 after transplantation, the right auricle of each B6 mouse was treated with each test substance (TRP-2 (10 μg for one side of each auricle), Compound A-(1) (20 μL of 100 μM solution for one side of each auricle) by the same method as Example 3. Ten days later, the left auricle was treated in the same manner, and the mice in each experimental group were examined for mortality. Three experimental groups were established: (1) a group undergoing TS alone, (2) a group undergoing TS followed by application of Compound A-(1), and (3) a group undergoing TS followed by application of TRP-2 and Compound A-(1) (10 animals in each group).

[Results]

Changes over time in the number of surviving individuals (animals) in each experimental group are shown in Table 5.

TABLE 5

| The days after B16 melanoma cells inoculation | Experimental group (1) | Experimental group (2) | Experimental group (3) |
|---|---|---|---|
| 16 | 10 | 10 | 10 |
| 21 | 9 | 10 | 10 |
| 24 | 9 | 10 | 10 |
| 27 | 6 | 7 | 10 |
| 29 | 3 | 7 | 10 |
| 31 | 0 | 7 | 10 |
| 33 | 0 | 7 | 10 |
| 35 | 0 | 2 | 10 |
| 37 | 0 | 2 | 10 |
| 38 | 0 | 2 | 10 |
| 40 | 0 | 0 | 8 |
| 42 | 0 | 0 | 8 |
| 44 | 0 | 0 | 5 |
| 46 | 0 | 0 | 4 |
| 48 | 0 | 0 | 2 |
| 50 | 0 | 0 | 2 |
| 52 | 0 | 0 | 2 |
| 55 | 0 | 0 | 2 |
| 57 | 0 | 0 | 1 |

All animals in the experimental group (1) died by day 31, whereas many animals in the groups receiving an EP4 agonist survived beyond day 31; therefore, a life-prolonging effect of an EP4 agonist alone in the melanoma-inoculated mice was demonstrated. In the experimental group (3), in particular, all animals were alive even on day 38, demonstrating a remarkable life-prolonging effect; it was suggested that the life-prolonging effect may be enhanced by using an EP4 agonist and an antigen peptide in combination.

Formulation Examples

Formulation Example 1

Tablet

A solution (1000 ml) of 4-[(2-{(2R)-2-[(1E,3S)-4-(4-fluorophenyl)-3-hydroxybut-1-enyl]-5-oxopyrrolidine-1-yl}ethyl)sulfanyl]butanoic acid (250 mg) in ethanol, magnesium stearate (10 g), silicon dioxide (2000 mg), talc (1000 mg), and carboxymethylcellulose calcium (20 g) were admixed by conventional method, dried and then micro crystalline cellulose (500 g) added into the mixture and the total volume was adjusted to 1000 g. They were sufficiently admixed until they were equalized, and then punched out by conventional method to obtain 10000 tablets each containing 30 μg of active ingredient.

Formulation Example 2

Injection

α-cyclodextrin clathrate compound (600 mg) of methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate (50 mg) was dissolved into distilled water for injection (30 L), the solution was aseptic filtrated with membrane filter and then the solution 3 mL each was filled into a 5 mL capacity ampoule for injection to obtain injections (10000 ampoules) containing 5 μg of active ingredient.

Formulation Example 3

Patch

An adhesive liquid was prepared by dissolving a styrene-isoprene-styrene block copolymer (300 mg), an ultra-hypochromic rosin ester (300 mg) and a light liquid paraffin (400 mg) in ethyl acetate (Kishida Chemical Co., Ltd.) (1000 mg). A coating liquid was prepared by dissolving methyl 4-{[24 (1R,2R,3R)-3-hydroxy-2-{(1E,3S)-3-hydroxy-4-[3-(methoxymethyl)phenyl]but-1-enyl}-5-oxocyclopentyl)ethyl] sulfanyl}butanoate (40 mg) in the adhesive liquid. The coating liquid was spread on a backing layer to a thickness of about 60 μm using a Baker type applicator. The adhesive face was dried under a reduced pressure at room temperature for 18 hours. The dried adhesive face was covered with a release liner and cut appropriately, to obtain patches (the main component content: 0.2 mg/cm$^2$).

INDUSTRIAL APPLICABILITY

An EP4 agonist exhibits an immunopotentiating activity through the activation of a cytotoxic T cell, and is therefore useful for the prevention and/or treatment of cancer or a microorganism-mediated infection disease.

BRIEF DESCRIPTION OF THE DRAWINGS

FIG. 1 is a graph which shows the effect of suppression of melanoma growth in the experimental groups (1) to (4) of Example 3.

The invention claimed is:

1. A method for activating cytotoxic T cells in a mammal, comprising administering an effective amount of EP4 agonist selected from the group consisting of 11α,15α,-dihydroxy-9-oxo-16-(3-methoxymethylphenyl)-17,18,19,20-tetranor-3,7-dithiaprost-13E-enoic acid, 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid and methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate to the mammal.

2. The method according to claim 1, wherein the cytotoxic T cell activation is potentiation of immunity against a cancer and/or microbial infectious disease.

3. The method according to claim 2, wherein the cancer is one or more selected from among a digestive cancer, a skin cancer, a respiratory cancer, a urinary cancer, a liver cancer, and a pancreatic cancer.

4. The method according to claim 3, wherein the skin cancer is a melanoma.

5. The method according to claim 2, wherein the microorganism is one or more selected from among a virus, a bacterium, and a fungus.

6. The method according to claim 1, wherein the agent further comprises at least one antigen peptide.

7. The method according to claim 6, wherein the at least one antigen peptide is a melanoma-specific antigen peptide.

8. A method for treating a patient having a cancer comprising administering to the patient an effective amount of EP4 agonist selected from the group consisting of 11α,15α,-dihydroxy-9-oxo-16-(3-methoxymethylphenyl)-17,18,19,20-tetranor-3,7-dithiaprost-13E-enoic acid, 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid and methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate thereby to activate cytotoxic T cells.

9. The method of claim 8, wherein the EP4 agonist is administered to the patient, with a low prevalence of adverse effects, at a skin deprived of a corneal layer to potentiate immunity against a cancer.

10. The method of claim 8, wherein said cancer is a cancer selected from the group consisting of digestive cancer, skin cancer, respiratory cancer, urinary cancer, liver cancer, and pancreatic cancer.

11. The method of claim 10, wherein the skin cancer is a melanoma.

12. The method according to claim 1, wherein the EP4 agonist is 11α,15α,-dihydroxy-9-oxo-16-(3-methoxymethylphenyl)-17,18,19,20-tetranor-3,7-dithiaprost-13E-enoic acid.

13. The method according to claim 1, wherein the EP4 agonist is 4-[(2-{(2R)-2-[(1E,3S)-4-(4-fluorophenyl)-3-hydroxybut-1-enyl]-5-oxopyrrolidin-1-yl}ethyl)sulfanyl]butanoic acid.

14. The method according to claim 1, wherein the EP4 agonist is 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid.

15. The method according to claim 1, wherein the EP4 agonist is methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate.

16. The method according to claim 8, wherein the EP4 agonist is 11α,15α,-dihydroxy-9-oxo-16-(3-methoxymethylphenyl)-17,18,19,20-tetranor-3,7-dithiaprost-13E-enoic acid.

17. The method according to claim 8, wherein the EP4 agonist is 4-[(2-{(2R)-2-[(1E,3S)-4-(4-fluorophenyl)-3-hydroxybut-1-enyl]-5-oxopyrrolidin-1-yl}ethyl)sulfanyl]butanoic acid.

18. The method according to claim 8, wherein the EP4 agonist is 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid.

19. The method according to claim 8, wherein the EP4 agonist is methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate.

* * * * *